(12) United States Patent
Boiarski

(10) Patent No.: US 7,892,217 B2
(45) Date of Patent: Feb. 22, 2011

(54) VARIABLE CROSS-SECTION CONTAINMENT STRUCTURE LIQUID MEASUREMENT DEVICE

(75) Inventor: Tony Boiarski, Columbus, OH (US)

(73) Assignee: Future Path Medical, LLC, Columbus, OH (US)

( * ) Notice: Subject to any disclaimer, the term of this patent is extended or adjusted under 35 U.S.C. 154(b) by 726 days.

(21) Appl. No.: 11/367,822

(22) Filed: Mar. 3, 2006

(65) Prior Publication Data
US 2006/0229575 A1 Oct. 12, 2006

Related U.S. Application Data

(60) Provisional application No. 60/594,457, filed on Apr. 10, 2005.

(51) Int. Cl.
*A61M 1/00* (2006.01)
*G01F 23/00* (2006.01)
*G01F 23/24* (2006.01)

(52) U.S. Cl. .................. 604/318; 604/317; 73/290 R; 73/304 R

(58) Field of Classification Search ............... 604/317, 604/318; 73/290 R, 304 R
See application file for complete search history.

(56) References Cited

U.S. PATENT DOCUMENTS

| | | |
|---|---|---|
| 4,051,431 A | 9/1977 | Wurster |
| 4,343,316 A | 8/1982 | Jespersen |
| 4,390,073 A | 6/1983 | Rosen |
| 4,402,373 A | 9/1983 | Comeau |
| 4,417,585 A | 11/1983 | Frank |
| 4,447,939 A | 5/1984 | Taylor |
| 4,448,207 A | 5/1984 | Parrish |
| 4,449,969 A | 5/1984 | Schweizer |
| 4,501,144 A * | 2/1985 | Higashi et al. ........... 73/204.26 |
| 4,532,936 A | 8/1985 | LeVeen |

(Continued)

FOREIGN PATENT DOCUMENTS

EP  0 152 644 A2  8/1985

(Continued)

OTHER PUBLICATIONS

English translation of disclosure for JP 2002-156271 to Suzuki.*

(Continued)

*Primary Examiner*—Melanie J Hand
(74) *Attorney, Agent, or Firm*—Tarolli, Sundheim, Covell & Tummino LLP

(57) ABSTRACT

A liquid measurement device having a containment structure, a sensor, and an interface device, having particular applicability to the collection and administration of electrically conductive fluids. The device is configured to house and monitor the height of a fluid. The containment structure has at least one variable cross-section portion. The sensor has two cooperating variable resistance sections that account for the variable cross-section of the containment structure. The electrical resistance of the sensor changes as the fluid height changes and shorts out a portion of the sensor. The sensor may include an electrically conductive ink that is printed on the interior of the containment structure. The sensor receives an electrical measurement signal and modifies the signal in a predetermined manner to reflect the amount of fluid within the containment structure. The device is useful in measuring the amount of fluid in urine collection bags and intravenous bags.

39 Claims, 28 Drawing Sheets

U.S. PATENT DOCUMENTS

| | | | |
|---|---|---|---|
| 5,050,431 | A | 9/1991 | McDonald |
| 5,062,304 | A | 11/1991 | Van Buskirk |
| 5,115,193 | A * | 5/1992 | Bean et al. ............. 324/207.12 |
| 5,135,485 | A | 8/1992 | Cohen et al. |
| 5,148,708 | A | 9/1992 | Murata |
| 5,226,313 | A | 7/1993 | Murata |
| 5,312,379 | A | 5/1994 | Rahe |
| 5,351,036 | A * | 9/1994 | Brown et al. ................ 340/618 |
| 5,501,102 | A | 3/1996 | Williamson |
| 5,603,238 | A | 2/1997 | Williamson |
| 5,627,523 | A | 5/1997 | Besprozvanny et al. |
| 5,882,931 | A | 3/1999 | Peterson |
| 6,010,454 | A | 1/2000 | Afieff |
| 6,203,496 | B1 | 3/2001 | Gael |
| 6,360,612 | B1 * | 3/2002 | Trantzas et al. ............... 73/753 |
| 6,433,695 | B1 | 8/2002 | Kai |
| 6,595,051 | B1 | 7/2003 | Chandler, Jr. |
| 6,634,229 | B1 | 10/2003 | Kazkaz et al. |
| 2001/0018206 | A1 | 8/2001 | Delwiche |
| 2002/0161314 | A1 | 10/2002 | Sarajarvi |
| 2003/0158707 | A1 | 8/2003 | Doi |
| 2004/0081585 | A1 | 4/2004 | Reid |
| 2005/0214161 | A1 | 9/2005 | Gupta |

FOREIGN PATENT DOCUMENTS

| | | |
|---|---|---|
| JP | 11-100075 A | 4/1999 |
| JP | 2002-156271 A | 5/2002 |

OTHER PUBLICATIONS

Chambers, et al., Instruments for Sampling and Measuring the Volume Output of Urine from Grazing Female Sheep, Medical and Biological Engineering, Nov. 1976, pp. 665-670, U.S.

* cited by examiner

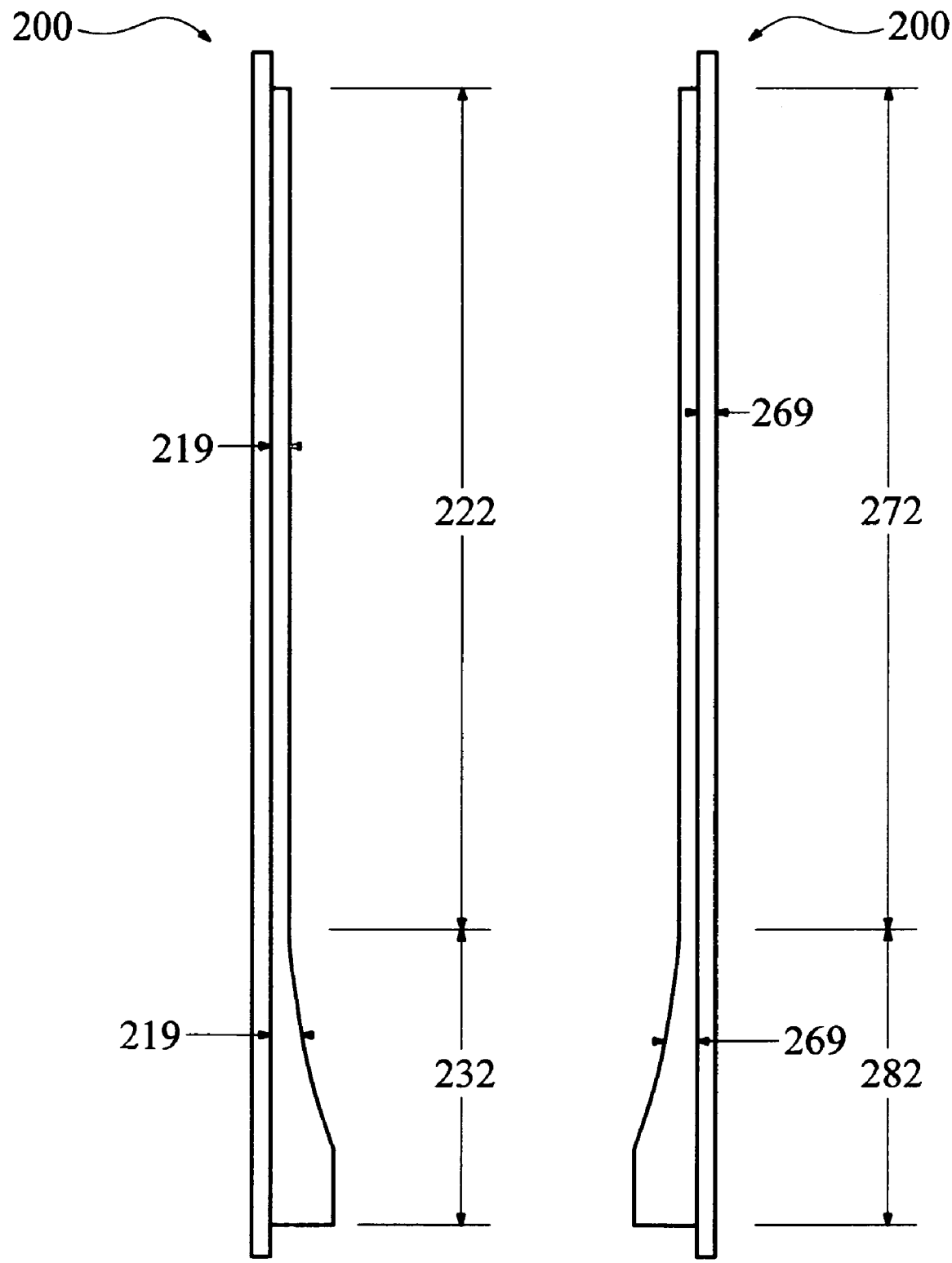

VARIABLE CROSS-SECTION CONTAINMENT STRUCTURE LIQUID MEASUREMENT DEVICE

CROSS-REFERENCE TO RELATED APPLICATIONS

This application claims the benefit of U.S. provisional patent application Ser. No. 60/594,457, filed Apr. 10, 2005, all of which is incorporated by reference as if completely written herein.

STATEMENT REGARDING FEDERALLY SPONSORED RESEARCH OR DEVELOPMENT

This invention was not made as part of a federally sponsored research or development project.

THE NAMES OF THE PARTIES TO A JOINT RESEARCH AGREEMENT

Not applicable.

TECHNICAL FIELD

The present invention generally relates to a fluid measurement systems, especially resistance based measurement systems having variable resistance sections to account for variable cross-section regions of the reservoir, or containment device.

BACKGROUND OF THE INVENTION

For a variety of reasons, it is desirable to supply fluids such as electrolytes or to or collect fluids from a patient in various settings including hospitals, nursing homes, private homes, or wheelchairs. For example, there are many instances of patient treatment where it is necessary to collect and determine, at all times, the accurate amount of expelled body fluids, such as urine, that is being passed or released by the patient. It is, in fact, conventional in hospitals to collect urine from certain patients to measure and monitor urine output. This is routinely done for post-operative patients as well as those with urologic disorders where, for example, urine output is directly related to renal function. This type of procedure for collecting, measuring and monitoring urine takes on extreme importance because, for example, sudden changes in urine flow, which can occur at any time, can indicate that there is a deteriorating clinical condition in the patient. Changes in urine output have been correlated with changes in cardiac output.

The invasive collection of urine and measurement of urine output are typically accomplished by first catheterizing the patient, i.e. a catheter is passed through the urethra of the patient into the bladder. The other end of the catheter is connected to a container or vinyl drainage bag through a length of flexible tubing attached to an inlet-barbed fluid port of the bag. Typically the bag is supported below the patient from the patient's bed or other support system such as a wheelchair, and urine drains by gravity from the patient through the flexible tubing and into the collection bag. For those patients who are mobile, this collection device or bag is called a leg bag, and those in a hospital bed would have what is called a bed bag. Bed bags are usually 2,000 ml in capacity and leg bags are 1,000 ml, 800 ml, 700 ml, or even smaller. In addition to monitoring urine output as a function of time, the reservoir of a collection bag fills to capacity at unpredicted intervals and someone must empty the bag so it can fill once again with urine. Patients can sometimes obstruct the flow of urine into the bag by lying on the drain tube. Further, if there is blood in the urine, blood clots can form that may obstruct the catheter. In these cases, no urine appears in the bag after an expected time period. Both a filled bag and blocked tube can cause urine backup and a backup could cause deleterious effect on the patient's condition. For all the above reasons, monitoring collection bags is an important part of providing effective patient therapy.

Prior art describes different types of systems that are employed to collect and measure urine output. For example, several systems use urine collection bags formed of a clear and flexible plastic (vinyl) material, which contain indicia in the form of graduations on the bag itself that represents the volume of the urine in the bag. In other systems the urine collection receptacle includes a rigid and clear plastic reservoir in fluid communication with a collection bag, which reservoir has volume related indicia and into which the urine initially flows and is stored prior to being emptied into the bag. See, for example, the urine meter bag described in U.S. Pat. No. 4,305,405.

These devices present several disadvantages. For example, there is a lack of accuracy in obtaining measurement readings that are made using the printed indicia and there is often a degree of difficulty in reading these devices depending on where they are positioned. Furthermore, the urinary output measurements and bag fill monitoring are dependent upon a person coming at precise time intervals to personally obtain and record bag fill data. This is often difficult to do. If the patient's room is dark a light must be turned on, disturbing the patient, and also disturbing their roommate in a double room.

There are several types of mechanical, electromechanical, and electronic devices used for metering, weighing and otherwise automatically monitoring and/or collecting body fluids, such as urine. Aside from the fact that many of these devices lack a certain degree of accuracy, they often present problems dealing with safety, high cost to manufacture and/or to operate, lack of portability and general difficulty of use. Many of these systems are often rendered inaccurate due to the influence of patient movement on the measuring or weighing device used within the system. This is particularly true because the patient is generally connected to the measuring or weighing device by flexible tubing, as seen, for example, in the systems described in U.S. Pat. Nos. 4,343,316; 4,390,073; 4,417,585; and 4,448,207.

It is also known in the art that medical offices having a fixed location and operational base can use ultrasound to measure the height of a column of urine in a rigid walled container and from that height measurement, the volume and volume flow rate of the urine is monitored. Urology doctors at their clinically controlled facilities gather controlled patient outputs to do incontinence assessments. These professional systems cost several thousands of dollars. Patients are typically scheduled for an office visit, and then a procedure is done for a medically controlled measurement and assessment of that patient's bladder and related urine production patterns.

SUMMARY OF THE INVENTION

In one of many general configurations, the present invention advances the state of the art with a variety of new capabilities and overcomes many of the shortcomings of prior devices in new and novel ways. The present invention overcomes the shortcomings and limitations of the prior art in any of a number of generally effective configurations. The instant invention demonstrates such capabilities and overcomes many of the shortcomings of prior methods in new and novel ways.

The present invention is a liquid measurement device having a containment structure, a sensor, and an interface device. The liquid measurement device is configured to house a fluid and monitor the fluid height of a fluid surface. Further, the liquid measurement device is in fluid communication with an external fluid channel so that the fluid may enter, or leave, the containment structure as dictated by the application.

The containment structure has an interior, for housing the fluid, a distal end, and a proximal end. Further, the containment structure has at least one containment wall, joining the containment structure distal end and the containment structure proximal end. Additionally, the containment structure has a containment structure length, which is the distance between the distal end and the proximal end. The containment structure has a port attached to the containment wall and configured to releasably connect to the external fluid channel.

The containment structure has at least one variable cross-section portion. The containment structure may also have a constant cross-section portion. The variable cross-section portion has a variable cross-section. Further, in embodiments having a constant cross-section portion, it has a constant cross-section.

The sensor is located within the containment structure interior. The sensor receives an electrical measurement signal and modifies the electrical measurement signal in a predetermined manner to reflect the amount of fluid within the containment structure. The sensor includes a primary portion and a secondary portion. Both the primary portion and the secondary portion each have a section that has a variable resistance. The introduction of variable resistance sections allows the sensor to account for the variable cross-section portion of the containment structure. The primary portion variable resistance section has a variable resistance section length wherein the resistance of the primary portion variable resistance section per unit length of the containment structure length varies over at least a portion of the length of the containment structure. Similarly, the secondary portion has a secondary portion variable resistance section. The secondary portion variable resistance section has a variable resistance section length wherein the resistance of the secondary portion variable resistance section per unit length of the containment structure length varies over at least a portion of the length of the containment structure.

The interface device has an interior interface portion located substantially in the containment structure interior and an exterior interface portion located substantially external to the containment structure. The interior interface portion is connected to a portion of the primary portion and a portion of the secondary portion. The measurement signal is transmitted through the containment wall between the interior interface portion and the exterior interface portion.

The sensor is located within the interior of the containment structure and components of the sensor, namely the primary portion and the secondary portion, and may come in contact with the fluid. The liquid level measurement is accomplished by having the fluid short out a portion of the primary portion and the secondary portion, such that the electrical resistance of the combination of these sections is changed, thereby modifying the electrical measurement signal in a predetermined manner to reflect the amount of fluid within the containment structure. The present invention allows for the continuous determination of the amount of fluid within a variable cross-section containment structure.

These variations, modifications, alternatives, and alterations of the various preferred embodiments, arrangements, and configurations may be used alone or in combination with one another as will become more readily apparent to those with skill in the art, with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

FIG. 8 is a right side elevation view of one embodiment of a sensor of the present invention, not to scale;

FIG. 9 is a right side elevation view of one embodiment of a sensor of the present invention, not to scale;

DETAILED DESCRIPTION OF THE INVENTION

Figure 1:
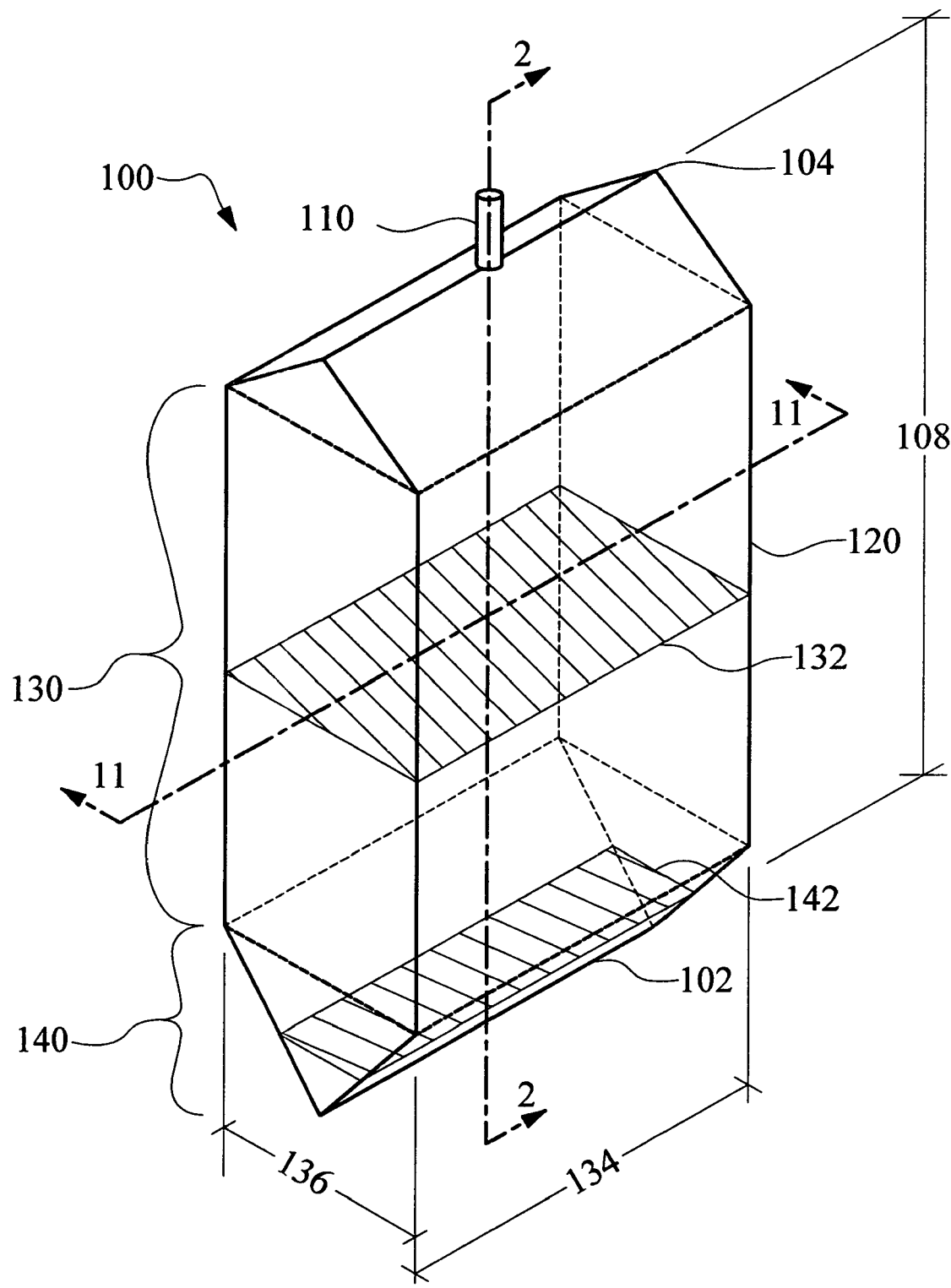
FIG. 1 is a perspective view of one embodiment of a containment structure of the present invention, not to scale.

The variable cross-section containment structure liquid measurement device of the instant invention, hereafter referred to as the liquid measurement device (1), enables a significant advance in the state of the art. The preferred embodiments of the apparatus accomplish this by new and novel arrangements of elements that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Referring generally to FIGS. 1 through 30, the present invention is a liquid measurement device (1) having a containment structure (100), a sensor (200), and an interface device (300). The liquid measurement device (1) is configured to house a fluid (10) and monitor the fluid height (14) of a fluid surface (12). Further, the liquid measurement device (1) is in fluid communication with an external fluid channel (500) so that the fluid (10) may enter, or leave, the containment structure (100) as dictated by the application. Accordingly, the port (110) may be located at the top, or proximal end (104), of the containment structure (10) or at the bottom, or distal end (102), of the containment structure (10).

Figure 2:
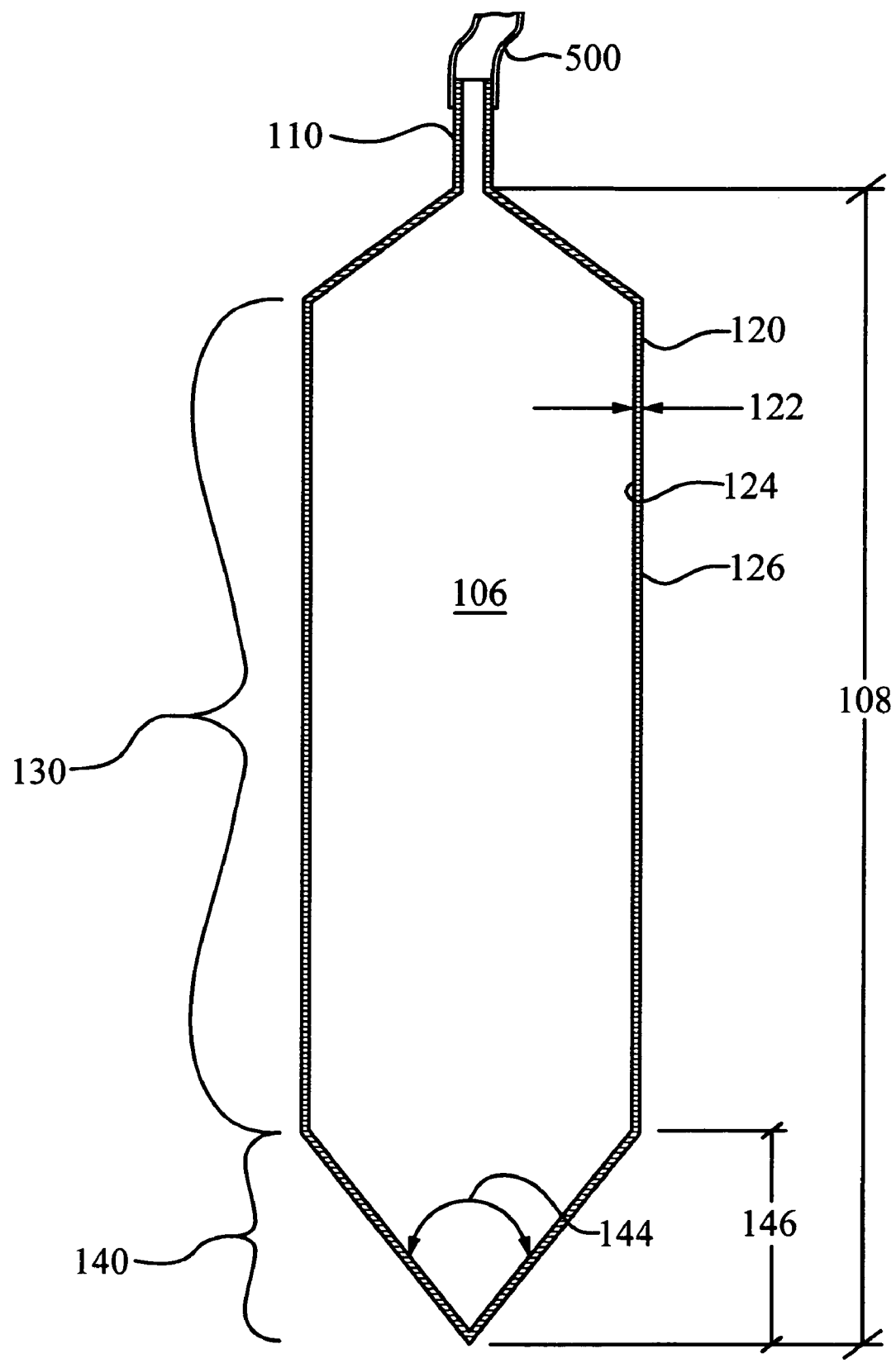
FIG. 2 is a cross-section view taken along section line 2-2 in FIG. 1, not to scale.
Figure 3:
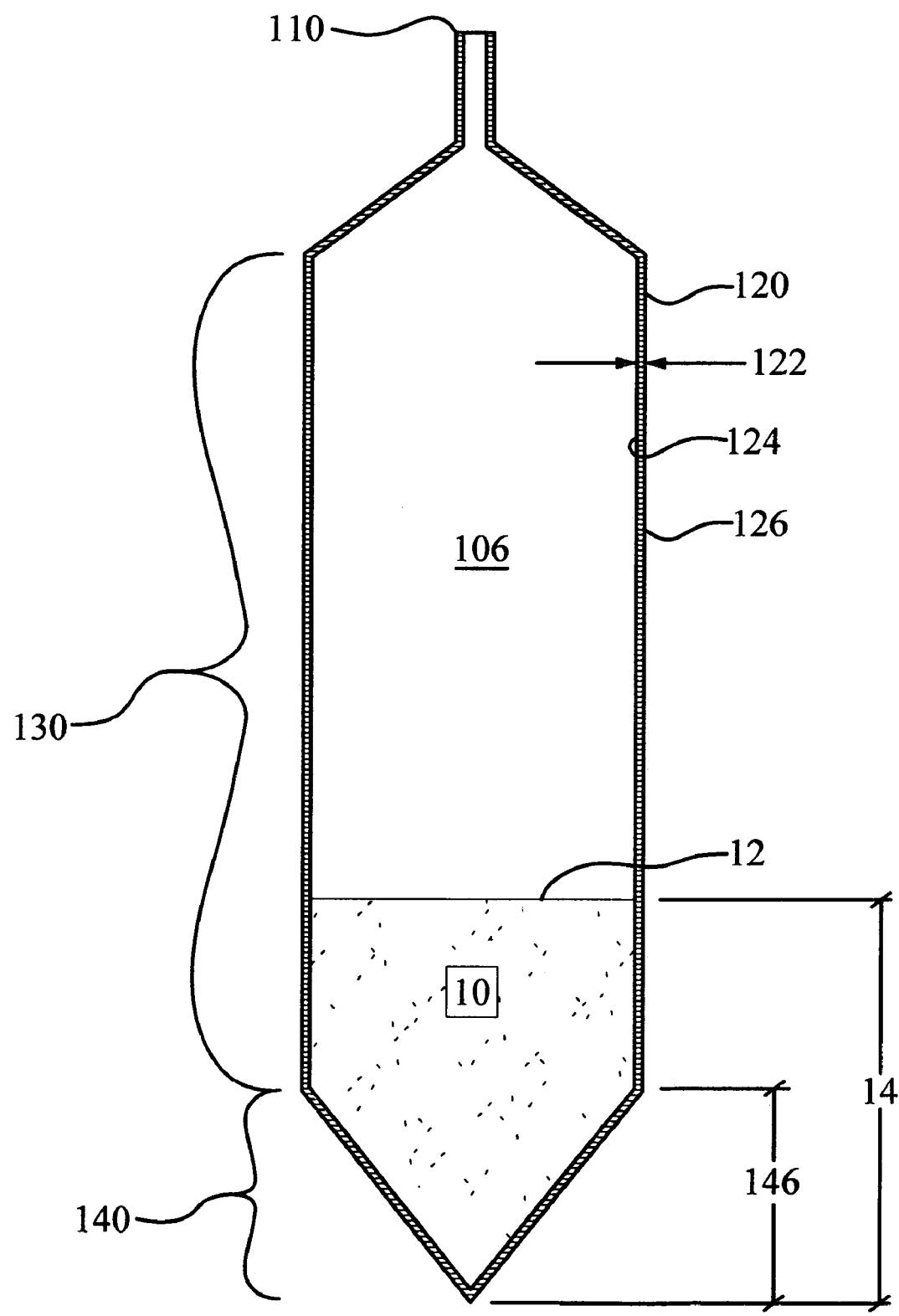
FIG. 3 is a cross-section view taken along section line 2-2 in FIG. 1, not to scale.

Now, the first of many embodiments of the present invention will be described. First, as seen in FIG. 1, the containment structure (100) has an interior (106), for housing the fluid (10), a distal end (102), and a proximal end (104). Further, the containment structure (100) has at least one containment wall (120), joining the containment structure distal end (102) and the containment structure proximal end (104). Additionally, the containment structure (100) has a containment structure length (108), which is the distance between the distal end (102) and the proximal end (104). With reference now to FIG. 2, the containment wall (120) has a wall thickness (122), an interior surface (124), and an exterior surface (126).

Figure 18:
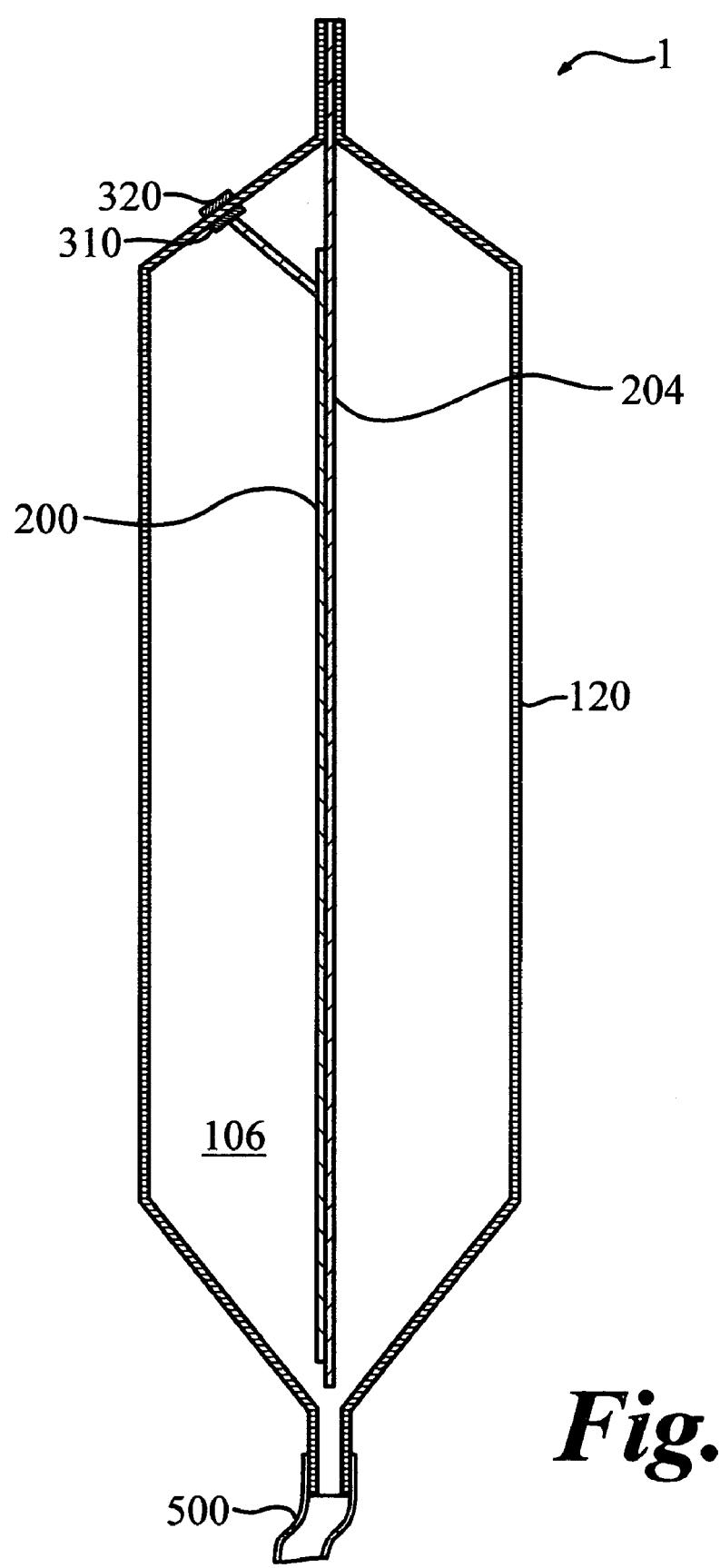
FIG. 18 is a cross-section view of another embodiment taken along section line 2-2 in FIG. 1, not to scale.

The containment structure (100) has a port (110) attached to the containment wall (120) and configured to releasably connect to the external fluid channel (500), seen only in FIGS. 2 and 18, thereby permitting fluid communication between the containment structure interior (106) and the exterior fluid channel (500). Referring back to FIG. 1, the containment structure (100) has at least one variable cross-section portion (140). In the particular embodiment of FIG. 1, the containment structure (100) also has a constant cross-section portion (130), although such is not required by the present invention, see FIGS. 29 and 30. The constant cross-section portion (130) has a constant cross-section (132), whereas the variable cross-section portion (140) has a variable cross-section (142). The variable cross-section portion (140) is formed by a convergence of the containment wall (120) at a convergence angle (144), seen in FIG. 2. It should be noted that the variable cross-section portion (140) need not be integral to the containment wall (120). In other words, the variable cross-section portion (140) may be joined to the constant cross-section portion (130), and need not be an integral extension of the containment wall (120). Additionally, the variable cross-section portion (140) has a transition length (146), seen in FIG. 3, which is the distance from the point at which the convergence of the containment wall (120) begins to the containment structure distal end (102). The fluid (10), fluid surface (12), and fluid height (14) are first illustrated in FIG. 3. The containment structure (100) is sealed from the exterior environment and is liquid-tight.

Secondly, with respect to the sensor (200), the sensor (200) is located within the containment structure interior (106), as seen in FIGS. 13-18. The sensor (200) receives an electrical measurement signal (202), illustrated only in the schematic of FIG. 23, and modifies the electrical measurement signal (202) in a predetermined manner to reflect the amount of fluid (10) within the containment structure (100). Now referring to FIG. 4, the sensor (200) includes a primary portion (210) and a secondary portion (260). The designation of the primary portion (210) and the secondary portion (260) is merely for convenience in describing the attributes of a particular portion of the sensor (200). Therefore, the sensor (200) is actually one continuous electrode that traverses the containment structure in a number of methods, as will be disclosed herein as a number of embodiments.

Both the primary portion (210) and the secondary portion (260) each have a section that has a variable resistance (230, 280) per unit length of the containment structure length (108). The introduction of variable resistance portions allows the sensor (200) to account for the variable cross-section portion (140) of the containment structure. In containment structure embodiments that have a constant cross-section portion (130) and a variable cross-section portion (140), both the primary portion (210) and the secondary portion (260) each have a section that has a constant resistance section (220, 270) and a section that has a variable resistance (230, 280).

Figure 4:
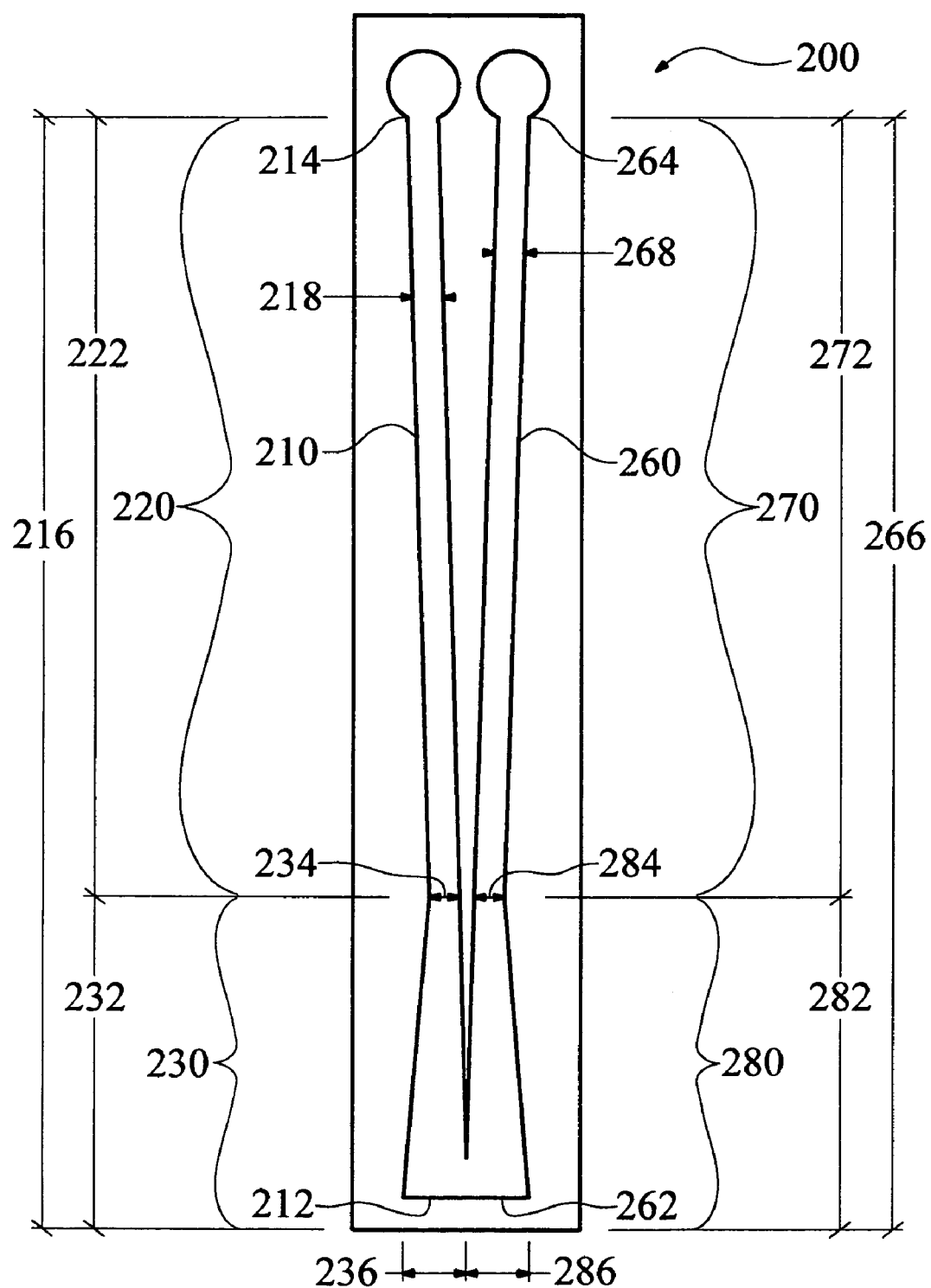
FIG. 4 is a front elevation view of one embodiment of a sensor of the present invention, not to scale.

With continued reference to FIG. 4, the primary portion (210) has a primary portion distal end (212), a primary portion proximal end (214), a primary portion length (216), a primary portion width (218), and a primary portion variable resistance section (230). In some embodiments the primary portion (210) further includes a primary portion constant resistance section (220). The primary portion constant resistance section (220) has a primary portion constant resistance section length (222) wherein the resistance of the primary portion constant resistance section (220) per unit length of the containment structure length (108) is substantially constant. The primary portion variable resistance section (230) has a variable resistance section length (232) wherein the resistance of the primary portion variable resistance section (230)

per unit length of the containment structure length (108) varies over at least a portion of the containment structure length (108).

Similarly, the secondary portion (260) has a secondary portion distal end (262), a secondary portion proximal end (264), a secondary portion length (266), a secondary portion width (268), and a secondary portion variable resistance section (280). In some embodiments the secondary portion (260) includes a secondary portion constant resistance section (270). The secondary portion constant resistance section (270) has a secondary portion constant resistance section length (272) wherein the resistance of the secondary portion constant resistance section (270) per unit length of the containment structure length (108) is substantially constant. The secondary portion variable resistance section (280) has a variable resistance section length (282) wherein the resistance of the secondary portion variable resistance section (280) per unit length of the containment structure length (108) varies over at least a portion of the containment structure length (108).

Figure 10:
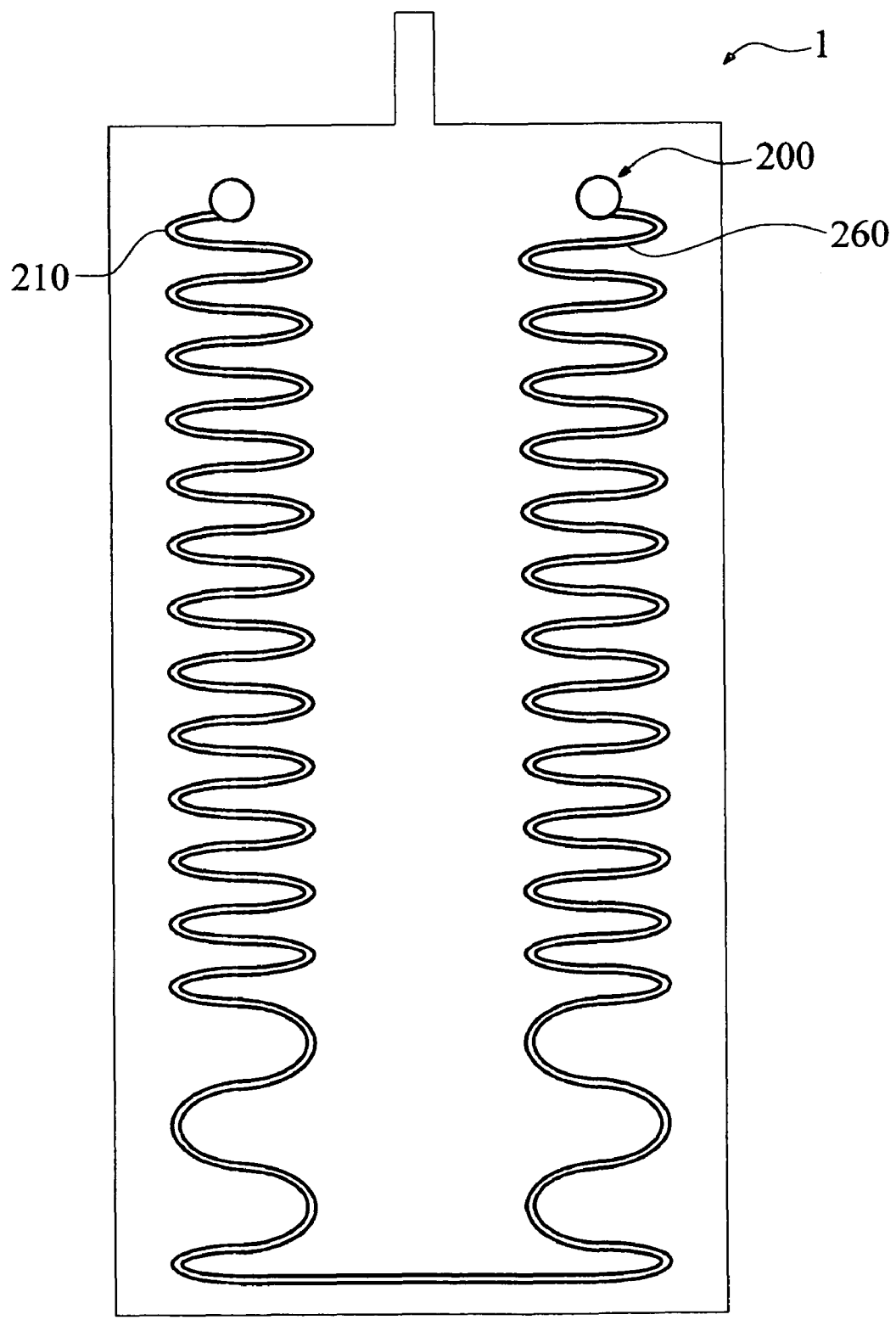
FIG. 10 is a front elevation view of one embodiment of a sensor of the present invention, not to scale.
Figure 22:
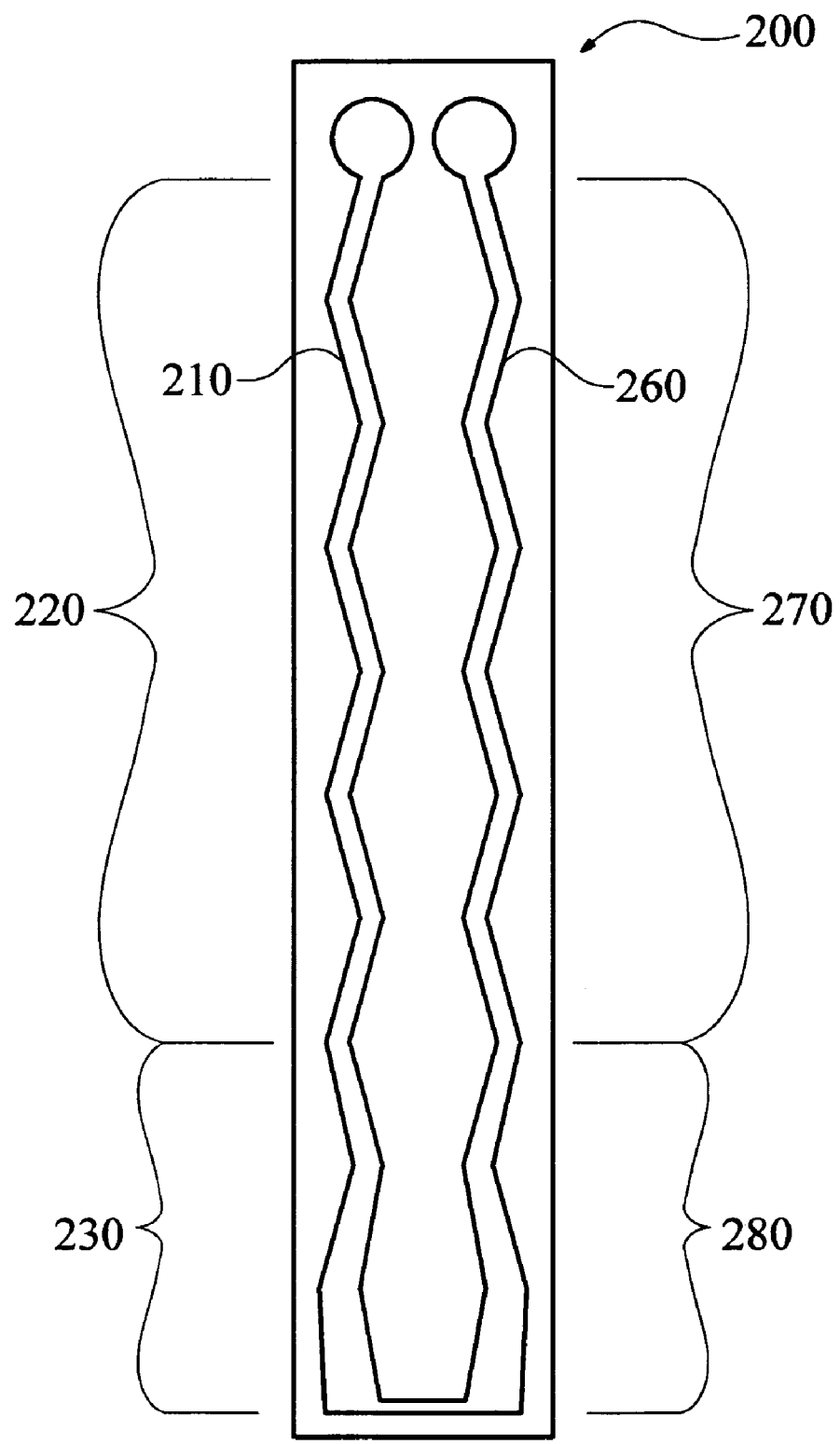
FIG. 22 is a front elevation view of one embodiment of a sensor of the present invention, not to scale.

As one with skill in the art will appreciate, the variable resistance per unit length of the containment structure length (108) may be achieved in a number of ways. For instance, the width (218, 268) of the sensor (200) may be varied over the containment structure length (108) to vary the resistance of the sensor (200) per unit length of the containment structure length (108), as seen in FIGS. 4, 7, and 22. Additionally, the thickness (219, 269) of the sensor (200) may be varied over the containment structure length (108) to vary the resistance of the sensor (200) per unit length of the containment structure length (108), as seen in FIGS. 5, 6, 8, and 9. Further, the amount of sensor (200) may be varied per unit length of the containment structure length (108) to achieve the described variable resistance per unit length, as seen in FIGS. 10, which may be thought of as the pattern with which the sensor (200) traverses the containment structure (100). Still further, the resistance may be varied by changing the composition of the sensor (200).

Figure 30:
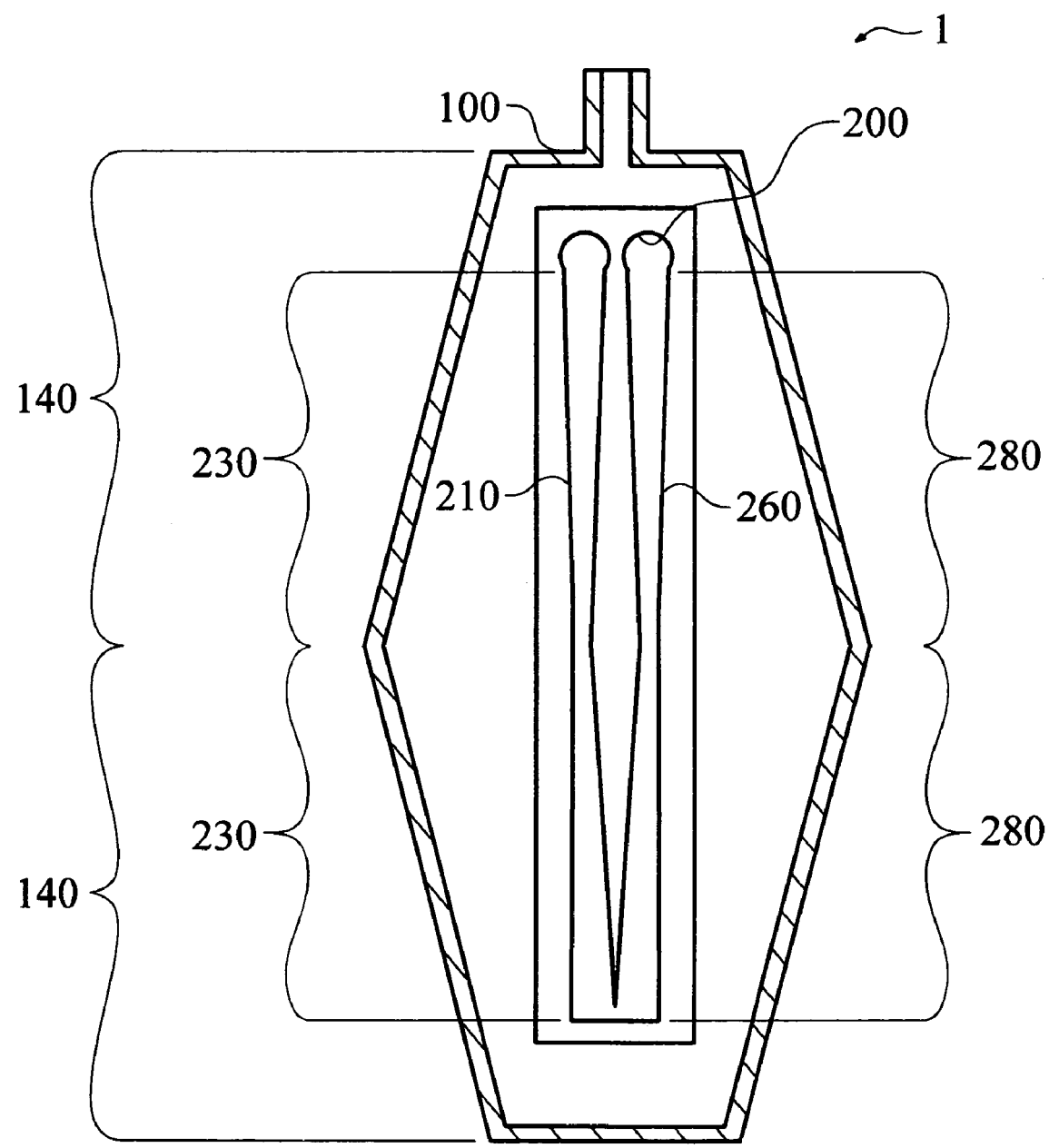
FIG. 30 is a cross-section view of a multiple variable cross-section portion embodiment of the present invention, not to scale.

First, one may focus on the embodiment in which the width (218, 268) is varied to create the primary portion variable resistance section (230) and the secondary portion variable resistance section (280), as seen in FIGS. 4, 7, and 22. In one embodiment both the primary portion (210) and the secondary portion (260) each have a section that has a constant width (220, 270) and a section that has a variable width (230, 280). However, one with skill in the art will recognize that if the containment structure (100) does not have a constant cross-section portion (130), in other words, has only a variable cross-section portion (140), then the constant resistance sections (220, 270) are not needed. For instance, a containment structure (100) having only a variable cross-section portion (140) is seen in FIG. 30. As such, in this embodiment, the primary portion (210) and the secondary portion (260) only have variable resistance sections (230, 280), and the constant resistant sections (220, 270) are absent. Further, a containment structure (100) having multiple variable cross-section portions (140) is seen in FIG. 31. In this embodiment, each portion (210, 260) may have multiple distinct variable resistance sections (230, 280) to account for the increasing, or decreasing, variable cross-section area.

The introduction of variable width portions allows the sensor (200) to account for the variable cross-section portion (140) of the containment structure (100). Thus, referring again to FIG. 4, the primary portion (210) has a primary portion distal end (212), a primary portion proximal end (214), a primary portion length (216), and a primary portion width (218). This embodiment includes a primary portion constant resistance section (220). The primary portion constant resistance section (220) is a primary portion constant width section, and the primary portion variable resistance section (230) is a primary portion variable width section. As previously mentioned, in this embodiment the primary portion constant resistance section (220) has a primary portion constant resistance section length (222) wherein the primary portion width (218) is substantially constant over the primary portion constant resistance section length (222) and/or the containment structure length (108). Additionally, the primary portion variable resistance section (230) has a primary portion variable resistance section length (232), a primary portion initiation width (234), and a primary portion termination width (236), wherein the primary portion width (218) varies over the primary portion variable resistance section length (232) and/or the containment structure length (108). In the embodiment of FIG. 4, the variation in the primary portion width (218) is linear, but that need not be the case, as seen in FIGS. 7, 13, 19, and 20.

Similarly, the secondary portion (260) has a secondary portion distal end (262), a secondary portion proximal end (264), a secondary portion length (266), and a secondary portion width (268). In the embodiment of FIG. 4, the secondary portion constant resistance section (270) is a secondary portion constant width section, and the secondary portion variable resistance section (280) is a secondary portion variable width section. As previously mentioned, in this embodiment the secondary portion constant resistance section (270) has a secondary portion constant resistance section length (272) wherein the secondary portion width (268) is substantially constant over the secondary portion constant resistance section length (272) and/or the containment structure length (108). Additionally, the secondary portion variable resistance section (280) has a secondary portion variable resistance section length (282), a secondary portion initiation width (284), and a secondary portion termination width (286), wherein the secondary portion width (268) varies over the secondary portion variable resistance section length (282) and/or the containment structure length (108).

Figure 5:
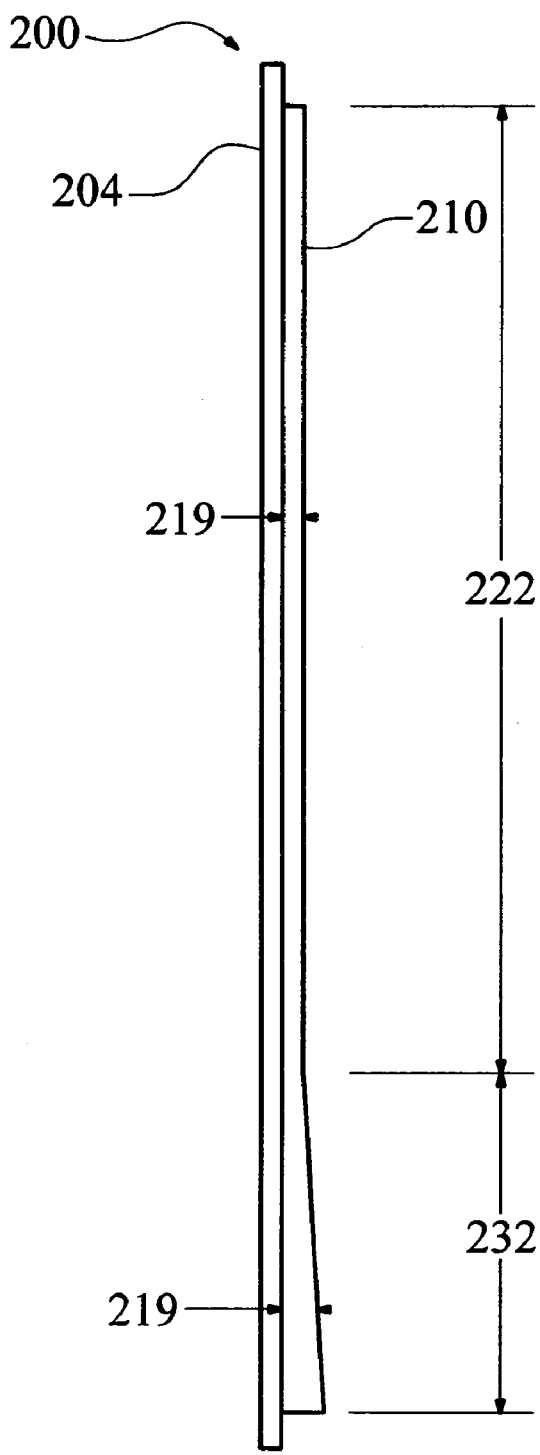
FIG. 5 is a right side elevation view of the embodiment of FIG. 4, not to scale.
Figure 6:
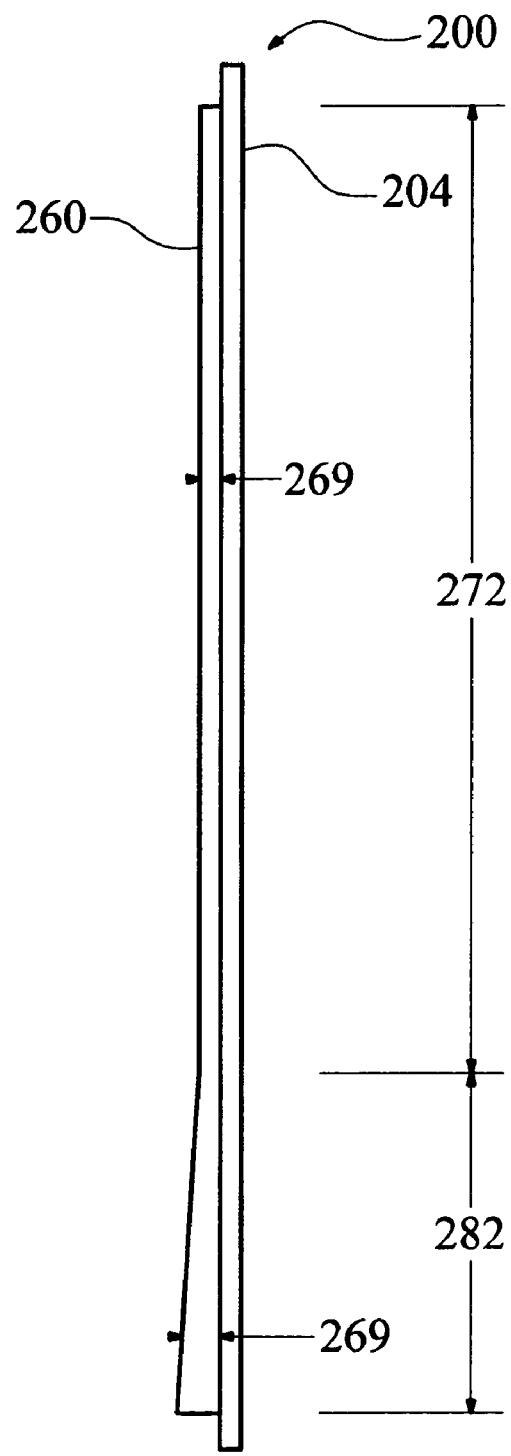
FIG. 6 is a left side elevation view of the embodiment of FIG. 4, not to scale.
Figure 7:
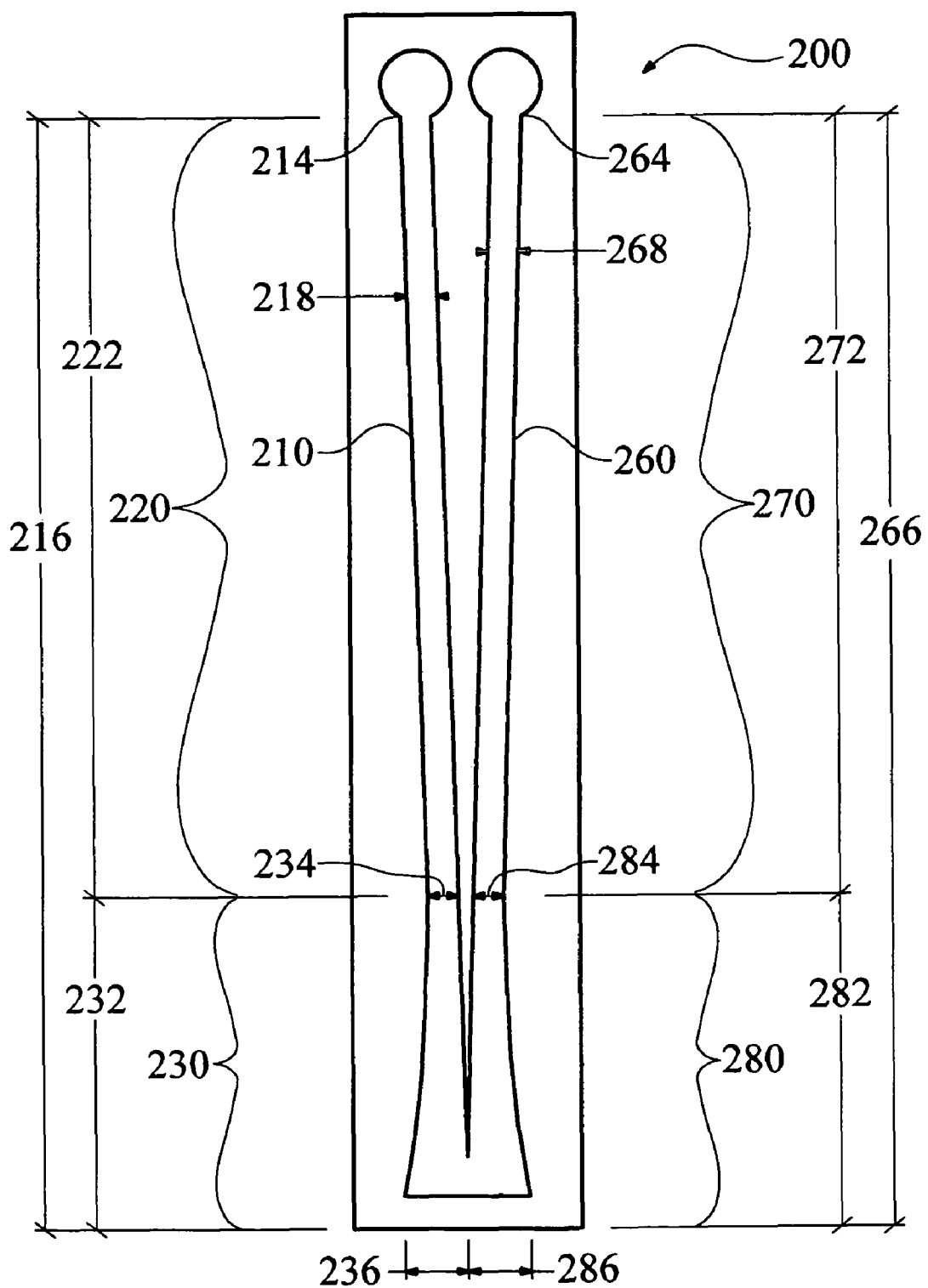
FIG. 7 is a front elevation view of one embodiment of a sensor of the present invention, not to scale.

Secondly, in the variable sensor thickness embodiment of FIGS. 5 and 6, the primary portion constant resistance section (220) is a primary portion constant thickness section, and the primary portion variable resistance section (230) is a primary portion variable thickness section. In this one embodiment the primary portion constant resistance section (220) has a primary portion constant resistance section length (222) wherein the primary portion thickness (219) is substantially constant over the primary portion constant resistance section length (222), and/or the containment structure length (108). Additionally, the primary portion variable resistance section (230) has a primary portion variable resistance section length (232) wherein the primary portion thickness (219) varies over at least a portion of the primary portion variable resistance section length (232) and/or the containment structure length (108). Similarly, in this embodiment, the secondary portion constant resistance section (270) is a secondary portion constant thickness section, and the secondary portion variable resistance section (230) is a secondary portion variable thickness section, as seen in FIGS. 5, 6, 8, and 9. In this embodiment the secondary portion thickness (269) is substantially constant over the secondary portion constant resistance section length (272) and the secondary portion thickness (269) varies over the secondary portion variable resistance section length (282), and/or the containment structure length (108). As one with skill in the art will appreciate, the variable width embodiment and the variable thickness embodiment are not mutually exclusive. In other words, the primary portion variable resistance section (230) may incorporate the variable width strategy, while the secondary portion variable resistance section (280) may incorporate the variable thickness strategy, and vice versa.

Thirdly, the amount of sensor (200), also thought of as the sensor path distance, may be varied per unit length of the containment structure length (108) to achieve the described variable resistance per unit length, as seen in FIG. 10. In other words, the variable resistance per unit length of the containment structure length (108) may be achieved when the sensor (200) has both constant width and constant thickness by increasing, or decreasing, the amount of the sensor (200), or sensor path distance, present per unit length of the containment structure length (108). This may be accomplished by simply increasing, or decreasing, the primary portion length (216) or the secondary portion length (266) per inch of length of the containment structure (100). In one embodiment wherein the sensor (200) is oriented as a wave function of constant amplitude, seen in FIG. 10, this involves simply changing the period of a wave function to vary the resistance per unit length of the containment structure length (108). One with skill in the art will recognize that the previously described wave function embodiment is just one of numerous ways to achieve the desired result.

Figure 19:
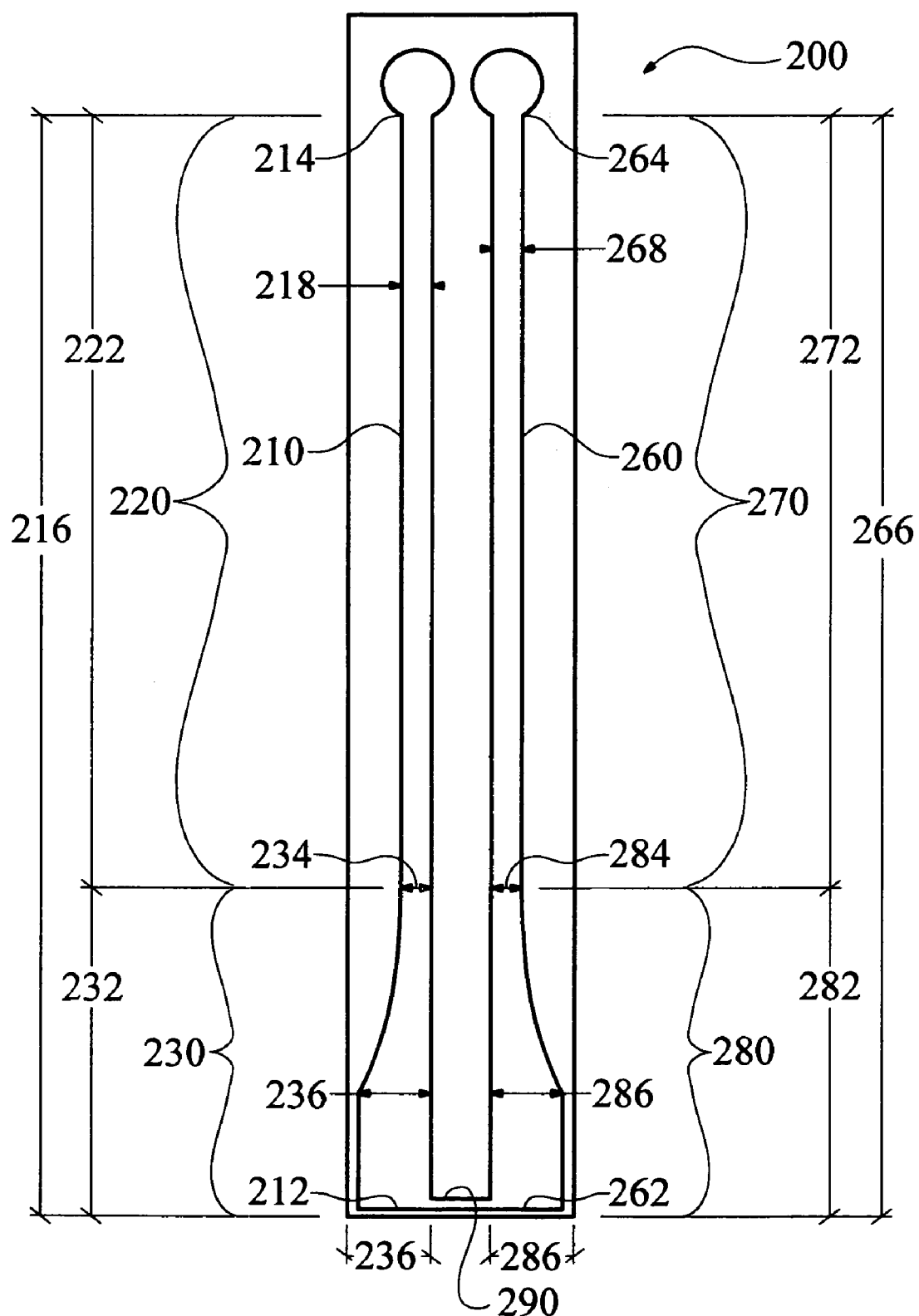
FIG. 19 is a front elevation view of one embodiment of a sensor of the present invention, not to scale.
Figure 20:
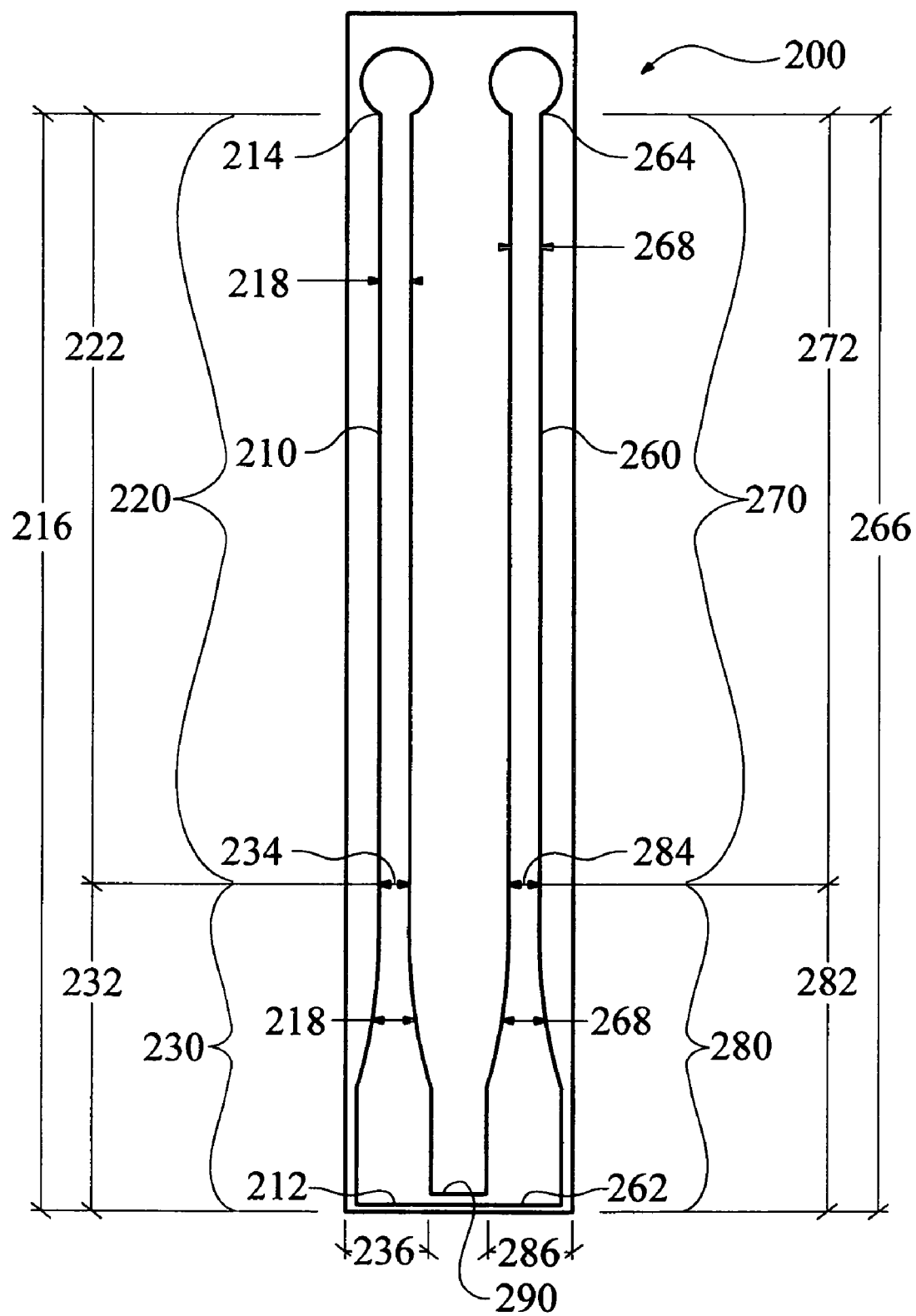
FIG. 20 is a front elevation view of one embodiment of a sensor of the present invention, not to scale.
Figure 21:
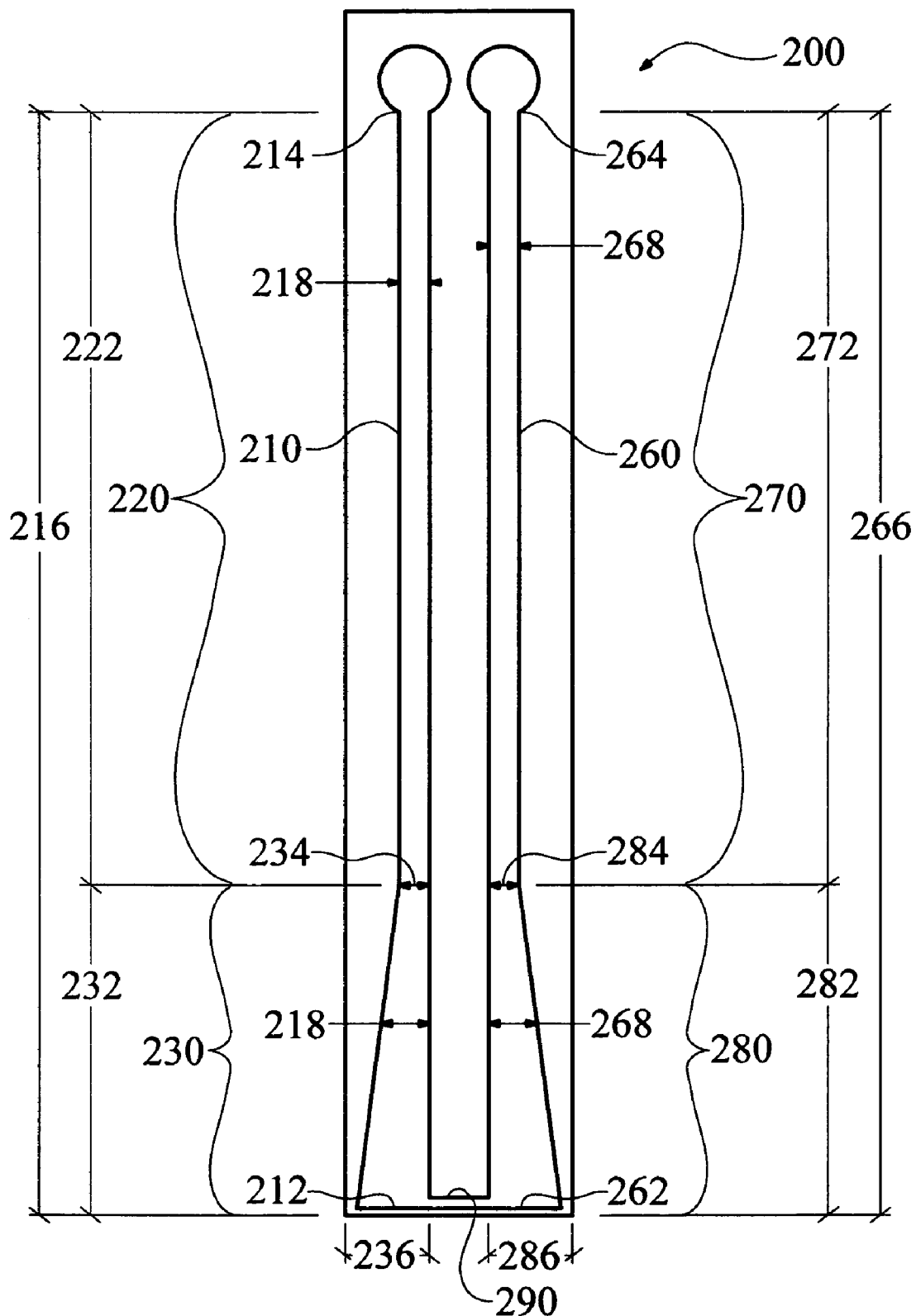
FIG. 21 is a front elevation view of one embodiment of a sensor of the present invention, not to scale.

As will be discussed in greater detail later herein, the widths (218, 268) and thickness (219, 269) of the variable resistance sections (230, 280) may change in any number of ways. For instance, the width (218, 268) may change linearly, as seen in FIGS. 4, 21, and 22, or the changes in width (218, 268) may incorporate one, or more, curved edges of the section (210, 260), as seen in FIGS. 7, 19, and 20. Similarly, the thicknesses (219, 269) may change linearly, as seen in FIGS. 5 and 6, or the change in thickness (219, 269) may incorporate a curved profile, as seen in FIGS. 8 and 9.

Figure 14:
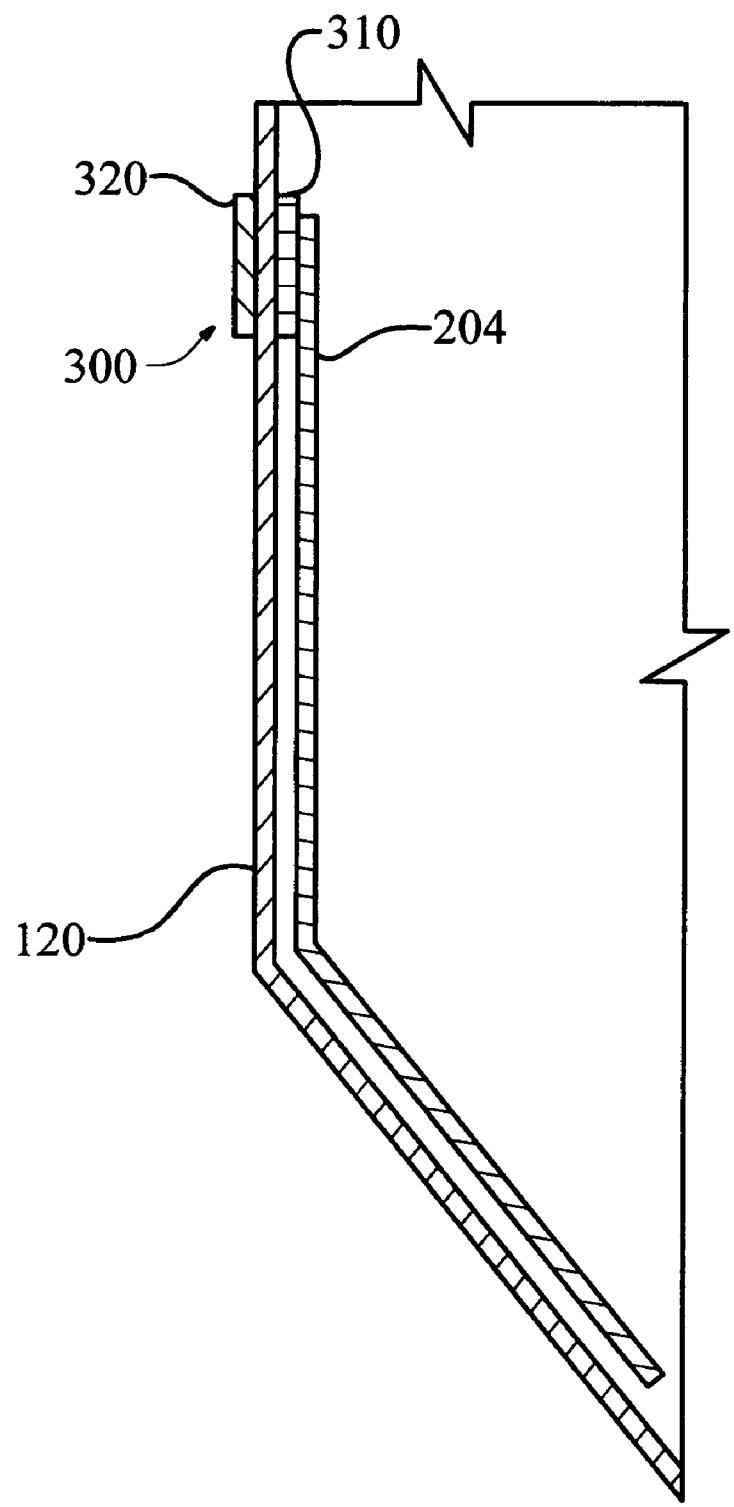
FIG. 14 is a partial cross-section view of one embodiment taken along section line 14-14 in FIG. 13, not to scale.

Thirdly, with respect to the interface device (300) of FIG. 14, the interface device (300) has an interior interface portion (310) located substantially in the containment structure interior (106) and an exterior interface portion (320) located substantially external to the containment structure (100). The interior interface portion (310) is connected to a portion of the primary portion (210) and a portion of the secondary portion (260). The measurement signal (202) is transmitted through the containment wall (120) between the interior interface portion (310) and the exterior interface portion (320).

The interior and exterior interface portions (310, 320) may penetrate through the containment wall (120) in a leak resistant manner, or they may be coupled together in a non-contact manner. One particular embodiment, seen in FIGS. 16 and 17, incorporates a mechanical joining system consisting of one or more leak resistant electrically conductive snap members wherein the interior interface (310) is an internal snap attaching unit (316) and the external interface (320) is an external snap closure unit (326). In one particular embodiment, the external snap closure unit (326) may include a male stud section or a female socket section designed to cooperate with a cooperating snap unit (420) on a data acquisition device (400), described later herein.

Another embodiment transmits the measurement signal (202) through the containment wall (120) without either the interior interface portion (310) or the exterior interface portion (320) penetrating the containment wall (120). In this non-penetrating embodiment, the interface device (300) communicates information from the sensor (200) to an external device through the containment wall (120) using a non-contact coupling approach. In one embodiment, information is transmitted electrically across the containment wall (120) by using a pair of capacitors or inductors for the interface portions (310, 320). The interface portions (310, 320) may be positioned on the containment structure in any number of ways that would be known to one skilled in the art. For example, the interface portions (310, 320) may be attached to the containment structure adhesively, they may be magnetically attached to one another, or they may be permanently attached to the containment structure (100).

Figure 15:
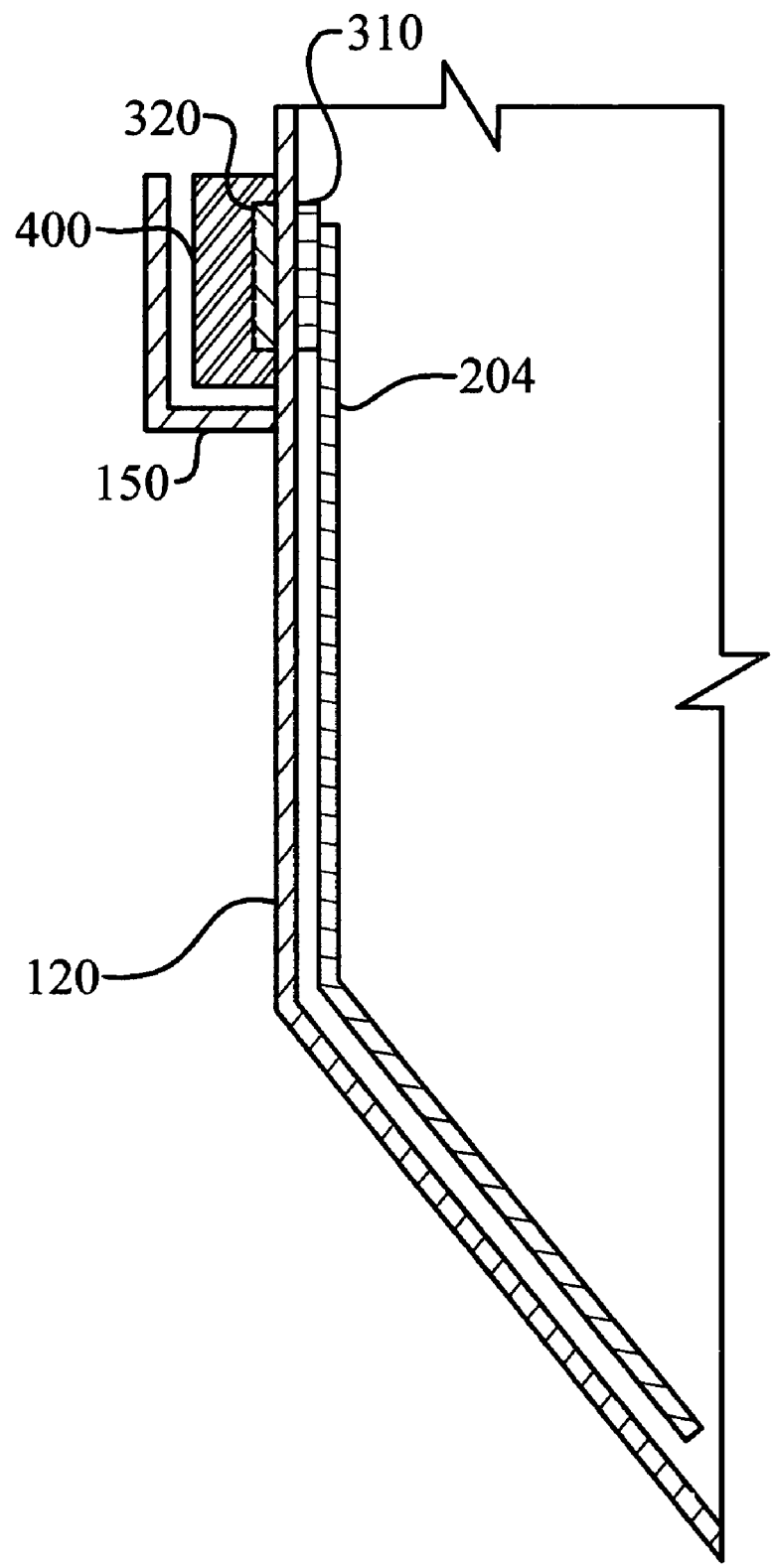
FIG. 15 is a partial cross-section view of another embodiment taken along section line 14-14 in FIG. 13, not to scale.
Figure 16:
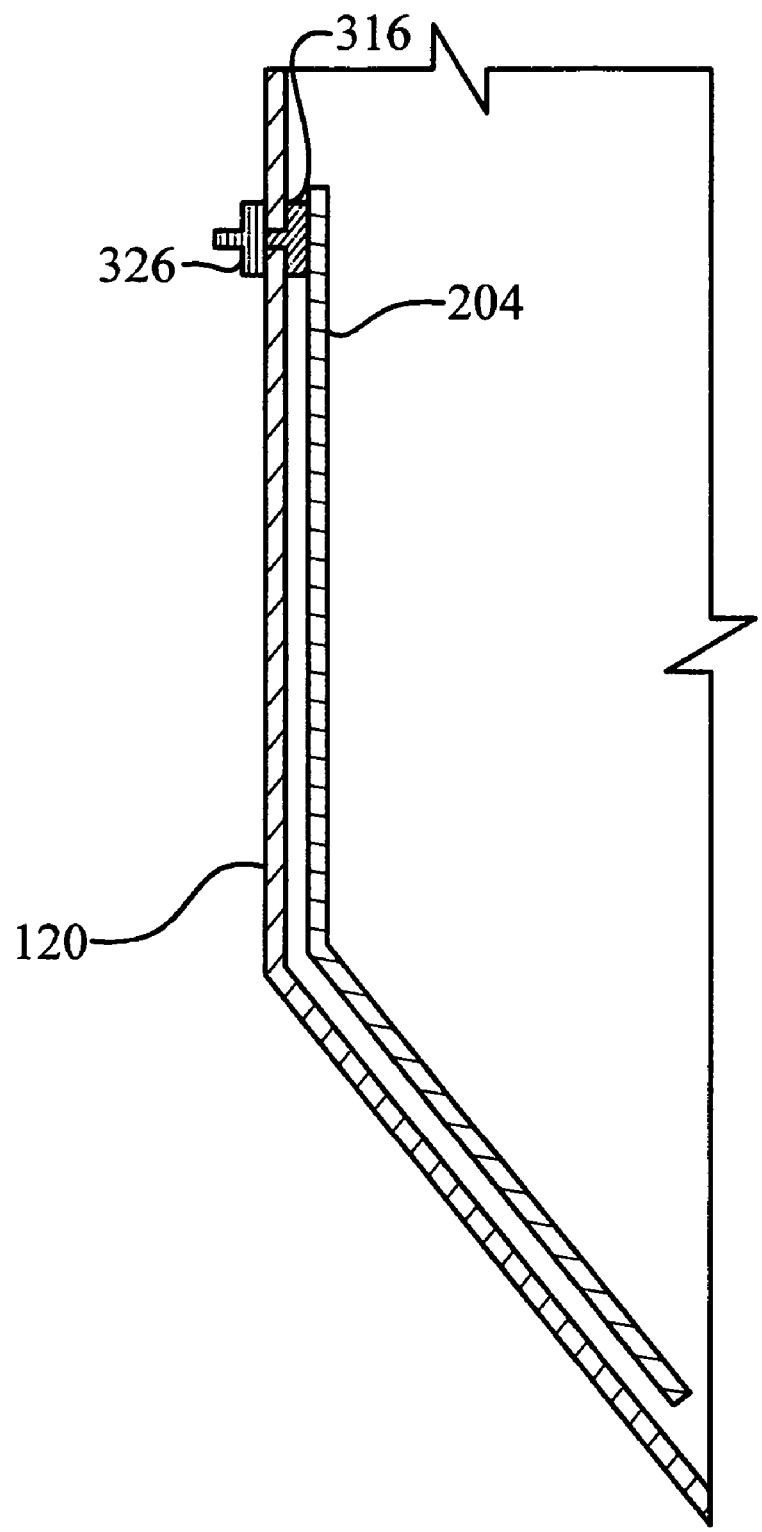
FIG. 16 is a partial cross-section view of another embodiment taken along section line 14-14 in FIG. 13, not to scale.
Figure 17:
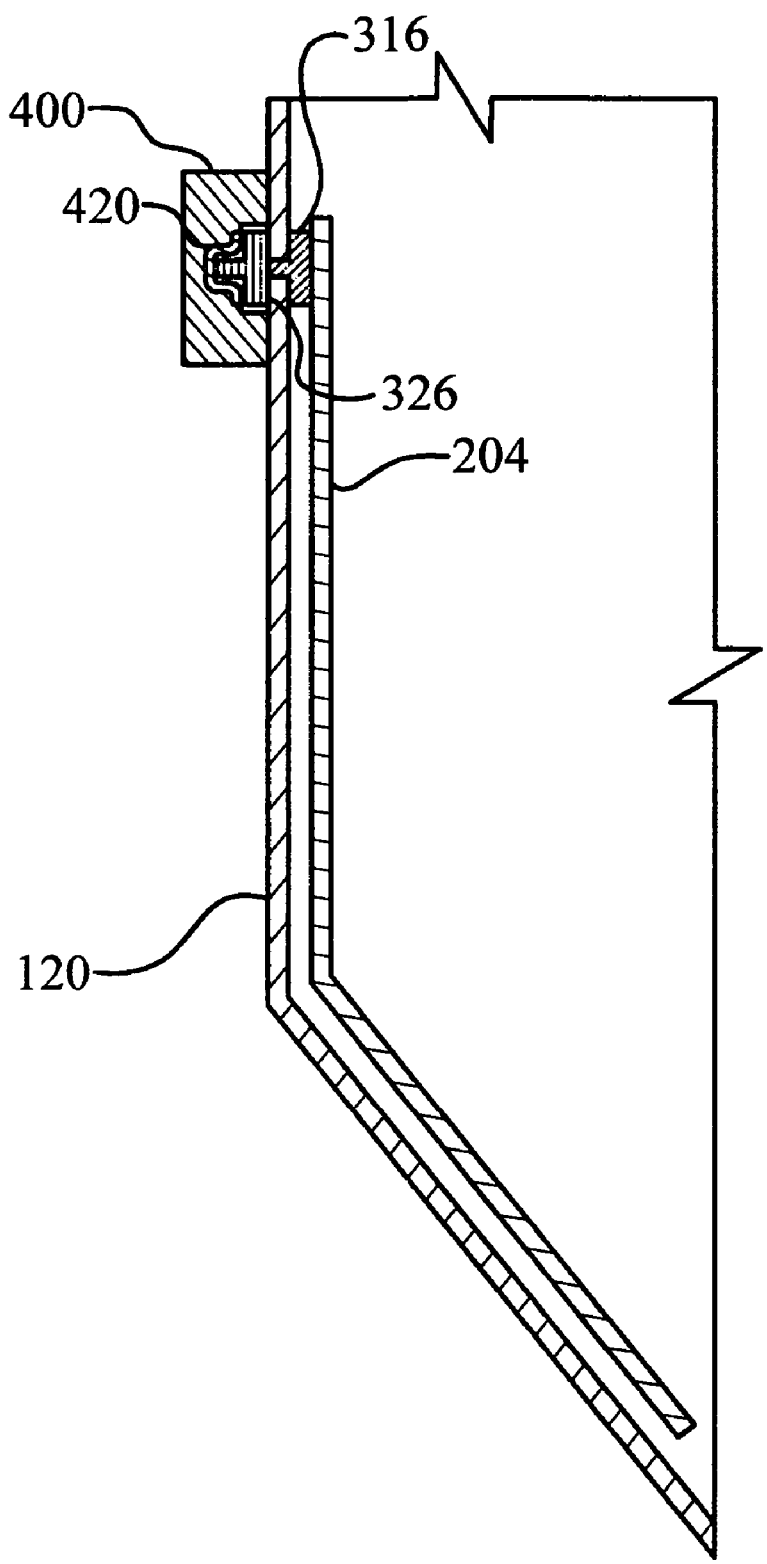
FIG. 17 is a partial cross-section view of another embodiment taken along section line 14-14 in FIG. 13, not to scale.

In one embodiment, seen in FIG. 15, the liquid measurement device (1) also includes a data acquisition device (400) in electrical communication with the interface device (300), wherein the data acquisition device (400) generates the measurement signal (202) and analyzes changes in the measurement signal (202). The data acquisition unit (400) may be battery powered, or hard-wired. The data acquisition unit (400) may include a display for indicating the volume of fluid in the containment structure (100). The data acquisition unit (400) may contain sensor transduction circuitry and a wireless transmitter to communicate sensor information to and from a portable readout unit located in the vicinity of the containment bag or a central monitoring station. The data acquisition device (400) may incorporate an alarm monitoring protocol whereby an alarm notifies a user if the fluid level has not changed in a predetermined fashion, and/or if a given fluid level has been reached. The portable readout unit may store and display higher order physiological fluid sensing and containment bag information, such as temperature, or pH. Additionally, the readout unit may warn the patient and caregivers of alarm conditions and can communicate sensing and alarm information to an external unit. The means of communication can be radio frequency (RF) or other standard methodology. The data acquisition device (400) may include at least one cooperating snap unit (420) that releasably attaches to the external interface portion (320), and more specifically to the external snap closure unit (326). In this embodiment, the at least one cooperating snap unit (420) establishes electrical communication between the data acquisition device (400) and the sensor (200), and the cooperation of the external snap closure unit (326) and the at least one cooperating snap unit (420) securely retains the data acquisition device (400) to the containment structure (100).

In yet another embodiment of the present invention, seen in FIG. 19, the sensor (200) includes a shunt portion (290) connecting the primary portion distal end (212) to the secondary portion distal end (262). The shunt portion (290) has a shunt portion distal end, a shunt portion proximal end, and a shunt portion width. The shunt portion (290) provides a path for electrical communication between the primary portion (210) and the secondary portion (260) when fluid (10) is not present, to create a short, or continuous path or resistance, between the primary and secondary portions (210, 260). In one embodiment, the shunt portion (290) resistance should match the smallest volume to be indicated by the sensor. Thus, if the containment structure (100) is 1000 mL and it is desirable to detect 5 mL (0.5% of the volume) then the shunt portion (290) should have a resistance of 0.5% of the initial resistance of the sensor (200). For example, if the initial resistance of the sensor (200) is 89.5 kOhms, then the resistance of the shunt portion (290) should be approximately 450 Ohms. An advantage of a shunt portion (290) is that it provides a definite signal when the first small amount of fluid flows into the containment structure (100).

Figure 11:
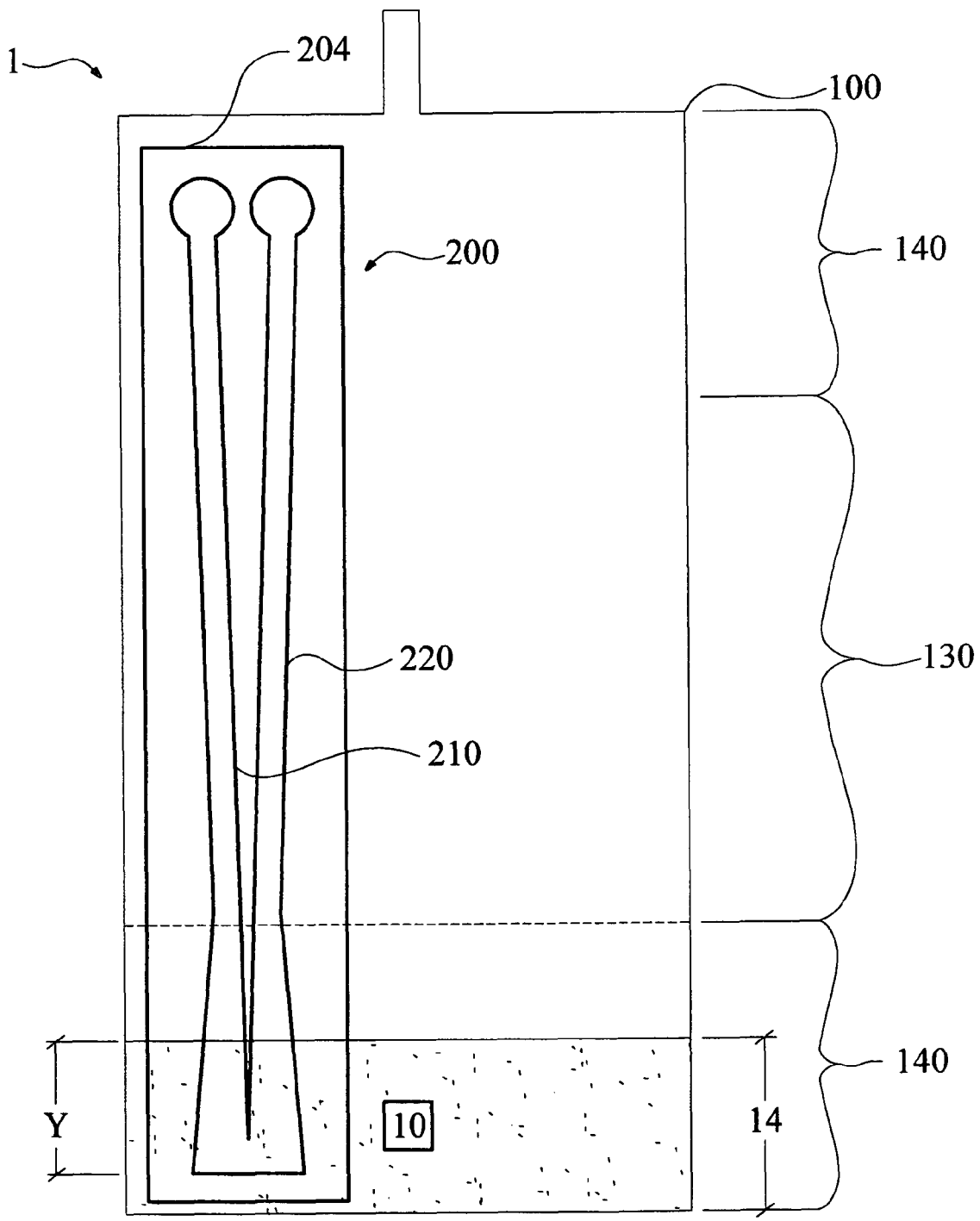
FIG. 11 is a cross-section view taken along section line 11-11, in FIG. 1, of one embodiment of the containment structure including the sensor embodiment of FIG. 4, not to scale.
Figure 12:
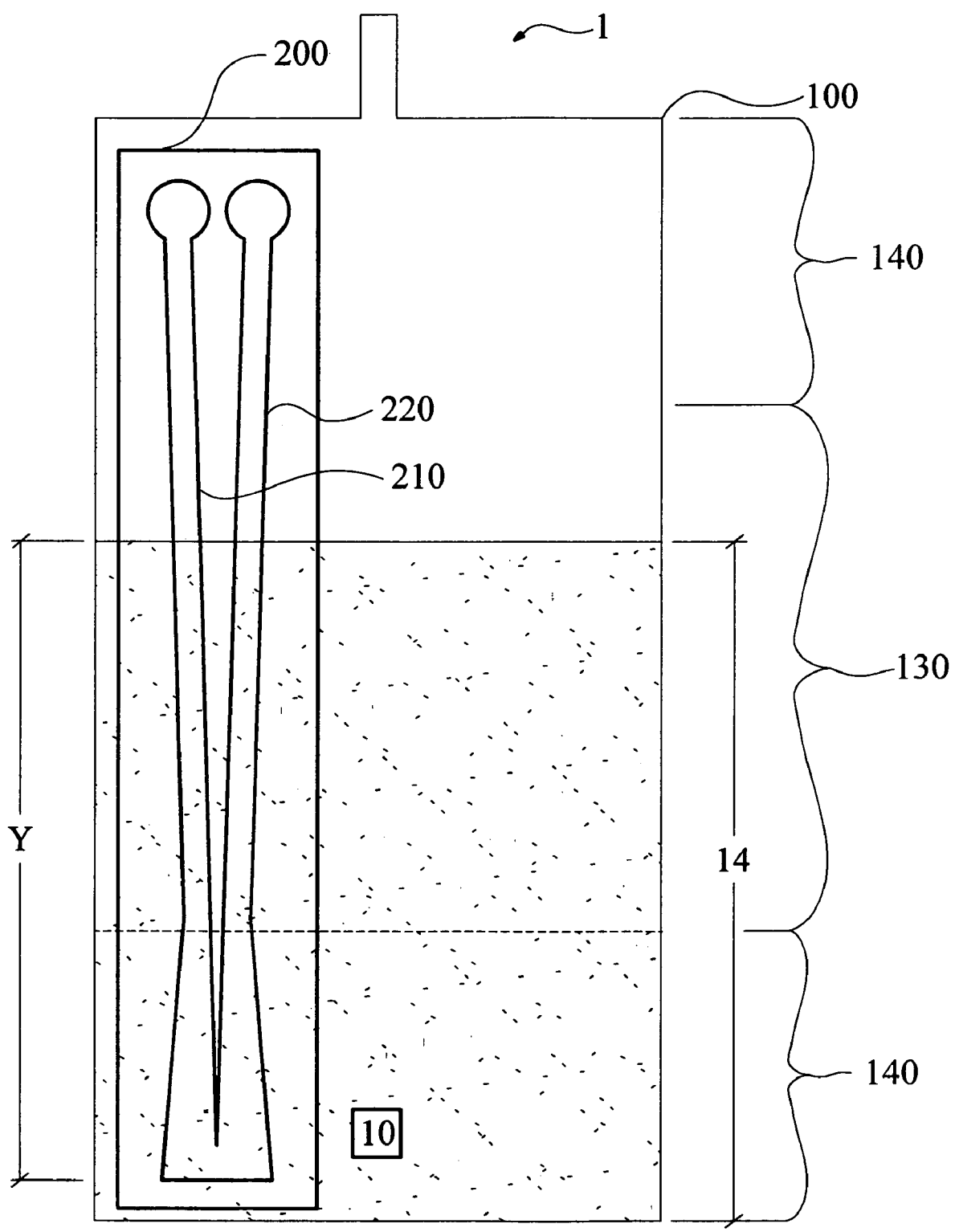
FIG. 12 is a cross-section view of one embodiment of the containment structure including the sensor embodiment of FIG. 4, not to scale.

Now, with the basic elements of one embodiment of the liquid measurement device (1) disclosed, a brief explanation of the benefits of the present invention, and the basis for such improvements over the prior art, is in order. The sensor (200) is located within the interior (106) of the containment structure (100) and components of the sensor (200), namely the primary portion (210) and the secondary portion (260), may come in contact with the fluid (10), as seen in FIGS. 11 and 12. The liquid level measurement is accomplished by having the fluid (10) short out a portion of the primary portion (210) and the secondary portion (260), such that the electrical resistance of the combination of these sections (210, 260) is changed, thereby modifying the electrical measurement signal (202) in a predetermined manner to reflect the amount of fluid (10) within the containment structure (10). These changes in the measurement signal (202) are readily measured.

The present invention allows for the continuous determination of the amount of fluid (10) within the containment structure (100). The resistance of the primary and secondary portions (210, 260) decreases as the fluid height (14) increases, as seen in FIGS. 11 and 12, thereby shorting out larger amounts of the primary and secondary portions (210, 260). This invention is independent of fluid density, temperature, and containment structure (100) pressure. The fluid (10) may be any conductive fluid. Generally, in a medical setting the fluid (10) will be urine, blood, or drainage fluid from a wound.

One with skill in the art will understand that the measured resistance between the primary portion (210) and the secondary portion (260) is high when no fluid (10) is present between the portions (210, 260), but the resistance between the primary and secondary portions (210, 260) drops to a low value equal to the resistance per centimeter of distance of the fluid (10) between the portions (210, 260) as physiological fluid covers the portions (210, 260). As one with skill in the art will appreciate, increasing the resistance of the primary and secondary portions (210, 260) will allow for a significantly greater distance between the primary and secondary portions (210, 260). In other words, increasing the resistance of the primary and secondary portions (210, 260) may allow the portions (210, 260) to be placed at locations in the containment structure (100) for manufacturing convenience, rather than directly adjacent to one another and only separated by a small distance. The large drop in resistance experienced when the primary and secondary portions (210, 260) are shorted together is be used to indicate the presence of the fluid (10) at a particular fluid height (14).

The primary and secondary portions (210, 260) may have sections insulated so that a particular insulated portion does not contact the fluid (10), or the portions may be totally exposed to the fluid (10). In one particular embodiment the primary and secondary portions (210, 260) are constructed such that the surface of the portions (210, 260) can contact the fluid (10) throughout the portion lengths (216, 266).

In another embodiment, primary and secondary portions (210, 260) are constructed of conductive ink, such as a carbon ink, that is either printed on the containment wall interior surface (124) or a sensor substrate (204) that is mounted within the containment structure (100). Such printing may be accomplished in virtually any fashion, however screen printing and ink-jet printing are commonly used. Carbon ink typically has a resistance value of 100-500 ohms per square. As those with skill in the art will recognize, for very thin films or materials, the term "ohms per square" means "ohms per unit area", in other words it could be "per square inch," "per square centimeter," etc. In this embodiment, the sensor substrate (204) may be a pliable material or a rigid material. A pliable sensor substrate (204) is beneficial in applications where the sensor (200) must be near the containment wall (120) so that the sensor (200) may bend with the shape of the containment structure (100). In fact, in some embodiments it is preferable to have the sensor substrate (204) constructed of the same material as the containment structure (100) so that it may be attached to the containment structure (100) without the addition of much additional rigidity to the structure (100). A rigid sensor substrate (204) may be preferable in embodiments in which the sensor (200) is generic, or not specific to one particular manufacturer of containment structures (100), so that the sensor (200) can be easily inserted into the containment structure (100) through the port (110).

In another embodiment, common for many urine collection bags in the medical field, the primary portion length (216) and the secondary portion length (266) are approximately 20 centimeters. In this embodiment, where space is a premium, it is desirable to minimize the distance between the primary and secondary portions (210, 260). In yet another embodiment, the primary portion width (218) and the secondary portion width (268) are selected to produce a resistance along the length of the primary portion (210) and the secondary portion (260) is in the order of approximately 1000 ohms per centimeter to approximately 6000 ohms per centimeter. As such, the primary portion width (218) and the secondary portion width (268) are commonly set at approximately 0.25 centimeters. However, it should be noted that one skilled in the art would appreciate that the primary and secondary portions (210, 260) could be located on opposite sides of the containment structure (100) and still provide accurate measurement results merely by increasing the resistance of the portions (210, 260) to account for the greater resistance of the short, i.e. the resistance of the fluid gap between the primary and secondary portions (210, 260).

Now, a more detailed explanation of the resistance of the sensor (200) is in order. The following detailed explanation is directed to an embodiment incorporating the sensor shunt portion (290), such as that of FIG. 21, however one skilled in the art will appreciate that the analysis methodology applies equally as well for embodiments that do not incorporate the shunt portion (290). First, equation 1 below identifies the resistance of the sensor ($R_{200}$) as being equal to the resistance of the shunt portion ($R_{290}$) plus the resistance of the primary portion ($R_{200}$) and the resistance of the secondary portion ($R_{260}$). It should be noted that $R_{200}$ is the resistance of element number 200, which is the entire sensor, therefore $R_{200}$ is the sensor resistance. Similarly, element number 290 is the shunt portion (290), thus $R_{290}$ is the resistance of the shunt portion. Further, element number 210 is the primary portion (210), thus $R_{210}$ is the resistance of the primary portion, and finally $R_{260}$ is the resistance of the secondary portion.

$$R_{200}=R_{290}+R_{210}+R_{260} \quad \text{(equation 1)}$$

Assuming that the primary and secondary portions (210, 260) are identical, equation 1 may be rewritten as:

$$R_{200}=R_{290}+2(R_{210}) \quad \text{(equation 2)}$$

As one with skill in the art will recognize, if the primary and secondary portions (210, 260) had one constant width over their entire lengths (216, 266) then the resistance of the primary portion ($R_{210}$) would simply be a matter of multiplying the resistance per unit length ($R_{UL}$) by the primary portion length (216), referred to in the equations below as $L_E$. Thus, the following equation applies for a sensor (200) having constant width sections (216, 266).

$$R_{200}=R_{290}+2(R_{UL})(L_E) \quad \text{(equation 3)}$$

Figure 23:
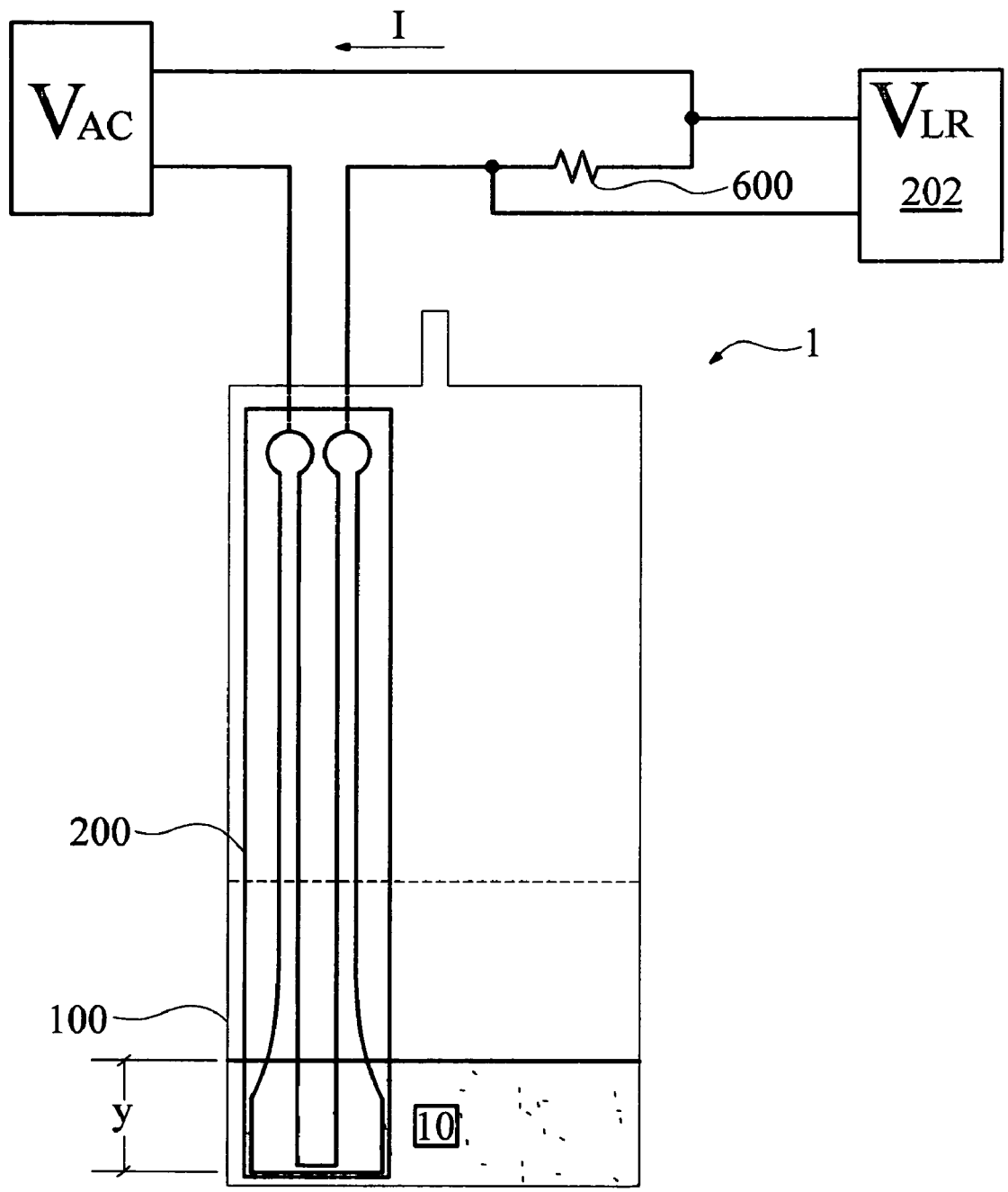
FIG. 23 is a an electrical schematic of one embodiment of the present invention, not to scale.

Then, as the fluid (10) rises a distance, referred to as "y", seen in FIG. 23, above the bottom of the shunt portion (290), an increasing amount of the primary and secondary portions (210, 260) are exposed to the fluid (10), thus creating a short between the primary and secondary portions (210, 260) and reducing the effective length of the sections (210, 260). The distance "y" may also be thought of as the length of the primary portion (210) that is covered with the fluid (10), therefore "y" will hereafter be referred to as the "portion wetted length." Thus, the resistance of the sensor ($R_{200}$) can be rewritten as a function of the portion wetted length (y) of the fluid above the bottom of the shunt portion (290), as follows.

$$R_{200}(y)=2(R_{UL})(L_E-y) \quad \text{(equation 4)}$$

The resistance of the shunt portion $R_{290}$ has disappeared from equation 4 because the short created by the fluid (10) removes the shunt portion (290) from the circuit. Further, equation 4 ignores the resistance of the fluid (10) because it is significantly less than the resistance of the sections (210, 260, 290), and doing so does not introduce any appreciable error. Simply put, equation 4 shows that the resistance of the sensor $R_{200}$ decreases by 2 times the resistance per unit length ($R_{UL}$) of the section for each centimeter increase in the portion wetted length (y).

Equation 4 can be simplified into the following equation:

$$R_{200}=R_E-K*y \quad \text{(equation 4a)}$$

where $R_{UL}$ and K are constants. For typical sensors fabricated to date, $R_E$=112,900 ohms and K=4,877 ohms/cm.

Thus, in instances in which the portion widths (218, 268) remains constant over the entire portion length (216, 266), the resistance of the sensor ($R_{200}$) decreases linearly with increases in the portion wetted length (y) of the fluid (10) above the shunt portion (290).

Measurement of the sensor resistance ($R_{200}$) can be made in various ways. For example, an electrical current (I) could be passed through the sensor (200) and the voltage drop across the sensor (200) could be measured. Alternatively, as seen in the electrical schematic of FIG. 23, a voltage source ($V_{AC}$) could be used in series with the sensor (200) and a fixed load resistor (600) having a resistance of $R_{600}$. Current (I) in the circuit will change with changing sensor resistance ($R_{200}$) and this current can be measured by measuring the voltage drop ($V_{LR}$) across the load resistor (600). The load resistor (600) will generally have a low resistance, such as 100 ohms. In any case, the electrical voltage or current source must alternate between positive and negative, fixed peak values (i.e., must be an alternating or AC source). A constant (i.e., fixed DC source) will not provide accurate data for an ionic (i.e., physiological) liquid.

In such an embodiment incorporating a load resistor (600), the current (I) in the circuit, given by Ohm's law, is:

$$I=V_{AC}/(R_{600}+R_{200}) \quad \text{(equation 5)}$$

Where $R_{200}$ is given by equation 4 above. The voltage drop ($V_{LR}$) across the load resistor (600) is:

$$V_{LR}=I(R_{600}) \quad \text{(equation 6)}$$

This load resistor voltage drop ($V_{LR}$) is easily measured and will now be referred to as a measurement signal (202), and denoted S in the following equations. As one with skill in the art will appreciate, the measurement signal (202) may be any number of electrical characteristics, including voltage, current, inductance, etc. The value of the measurement signal (202, S), as a function of portion wetted length (y) is given by the following Ohm's law based equation:

$$S(y)=I(R_{600})=V_{AC}(R_{600})[R_{600}+R_{200}(y)] \quad \text{(equation 7)}$$

Then inverting equation 7, yields:

$$1/S(y)=[R_{600}+R_{200}(y)]/(V_{AC}*R_{600}) \quad \text{(equation 8)}$$

Then, equation 8 can be simplified with the substitution of equation 4 to yield:

$$1/S(y)=[R_{600}+2(R_{UL})(L_E-y)]/V_{AC}*R_{600} \quad \text{(equation 9)}$$

Further simplifying equation 9 yields:

$$1/S(y)=[(1/V_{AC})+2(R_{UL})(L_E)/(V_{AC}*R_{600})]-[2(R_{UL})/(V_{AC}*R_{600})]*y \quad \text{(equation 10)}$$

Now, solving equation 10 for the fluid level (y) yields:

$$y=\text{SLOPE}*[1/S(y)]+\text{INTERCEPT} \quad \text{(equation 11)}$$

Where:

$$\text{SLOPE}=-V_{AC}*R_{600}/2(R_{UL}) \quad \text{(equation 12)}$$

With the SLOPE having units of Volt*cm, and $$\text{INTERCEPT}=L_E+(R_{600}/2(R_{UL})) \quad \text{(equation 13)}$$

With the INTERCEPT having units of centimeters.

Thus, the fluid level (y) changes linearly with the inverse of the measurement signal (202), (S(y)). Equation 11 can be rearranged to arrive at:

$$1/S(y)=\text{SLOPE}*y+\text{INTERCEPT} \quad \text{(equation 14)}$$

Figure 13:
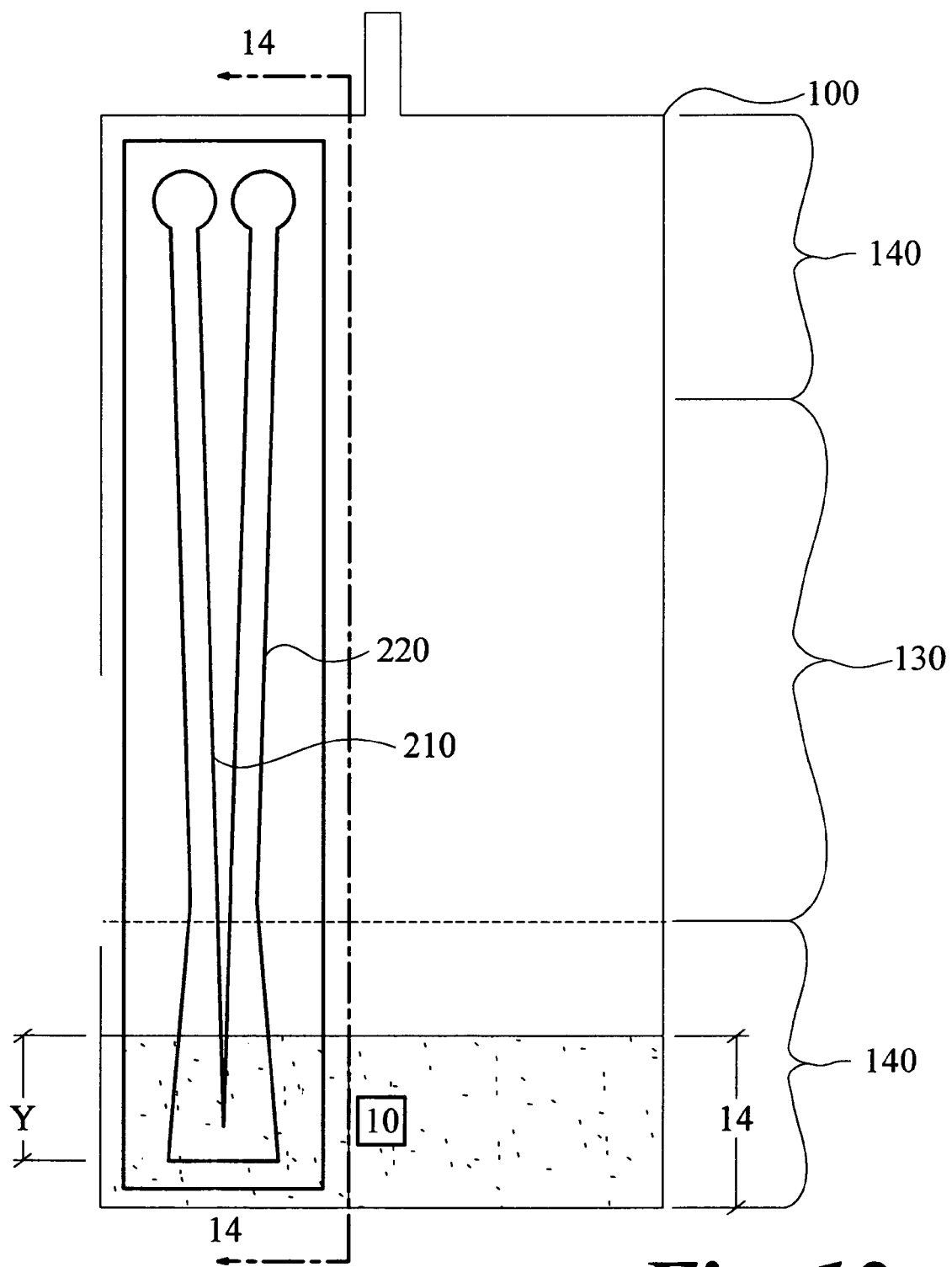
FIG. 13 is a cross-section view of one embodiment of the containment structure including the sensor embodiment of FIG. 4, not to scale.

For the schematic configuration of FIG. 13, with $V_{AC}$=11.2 volts AC source, $R_{600}$=100 ohms, $R_{UL}$=2750 ohms/cm, and $L_E$=20 cm, the theoretical values, from equations 12 and 13, are a SLOPE of approximately 203.6 mV-cm, and an INTERCEPT of approximately 20.02 cm. A similar experiment was performed to produce a SLOPE of approximately 205.6 mV-cm, and an INTERCEPT of approximately 23.7 cm, thus comparing favorably with the theoretical values.

If the containment structure (100) has a constant cross-sectional area, then the liquid volume, designated VOL, in the container varies linearly with fill height such that VOL∝y. For such a simple container, equation 11 can simply be converted to measure volume instead of fill height by multiplying by an appropriate constant related to the constant container area.

In general, however, most medical applications, particularly in urine collection applications, the containment structures (100) do not have constant cross-sectional areas along the entire length of the containment structure (100). Typical urine bags (especially low-cost bags) are made of sheets of vinyl material and the bag is formed using radio-frequency (RF) welding techniques that result in a variable cross-sectional area near the bottom (and top) of the bag. In yet another embodiment, seen in FIG. 15, the containment structure (100) further includes an auxiliary mounting pocket (150) to releasably house the data acquisition device (400).

FIG. 1 shows that the bag's cross-sectional area changes with fluid height. Within the constant cross-section portion (130) the cross-section (132) is constant. Conversely, within the variable cross-section portion (140) the cross-section (142) varies with the fluid height. As previously disclosed, the variable cross-section portion (140) is characterized by the containment wall (120) converging to the distal end (102) at a convergence angle (144), represented in the equations as φ. The constant cross-section portion width (134) is designated W in the following equations, and the constant cross-section portion depth (136) is designated D in the following equations. Thus, the volume, designated VOL in the following equations, of the fluid (10) in the containment structure (100), as a function of fluid height (14), designated H in the following equations, can be written as:

$$\text{VOL}=W*H^2*\text{Tan}(\phi/2) \quad \text{(equation 15)}$$

for situations with the fluid height (14) in the variable cross-section portion (140). Further, when the fluid height

(14) is in the constant cross-section portion (130), the volume of the fluid (10) in the containment structure (100) can be written as:

$$VOL = W^*(\text{transition length})^2 * \text{Tan}(\phi/2) + (H - \text{transition length})(W)(D) \quad \text{(equation 16)}$$

Figure 24:
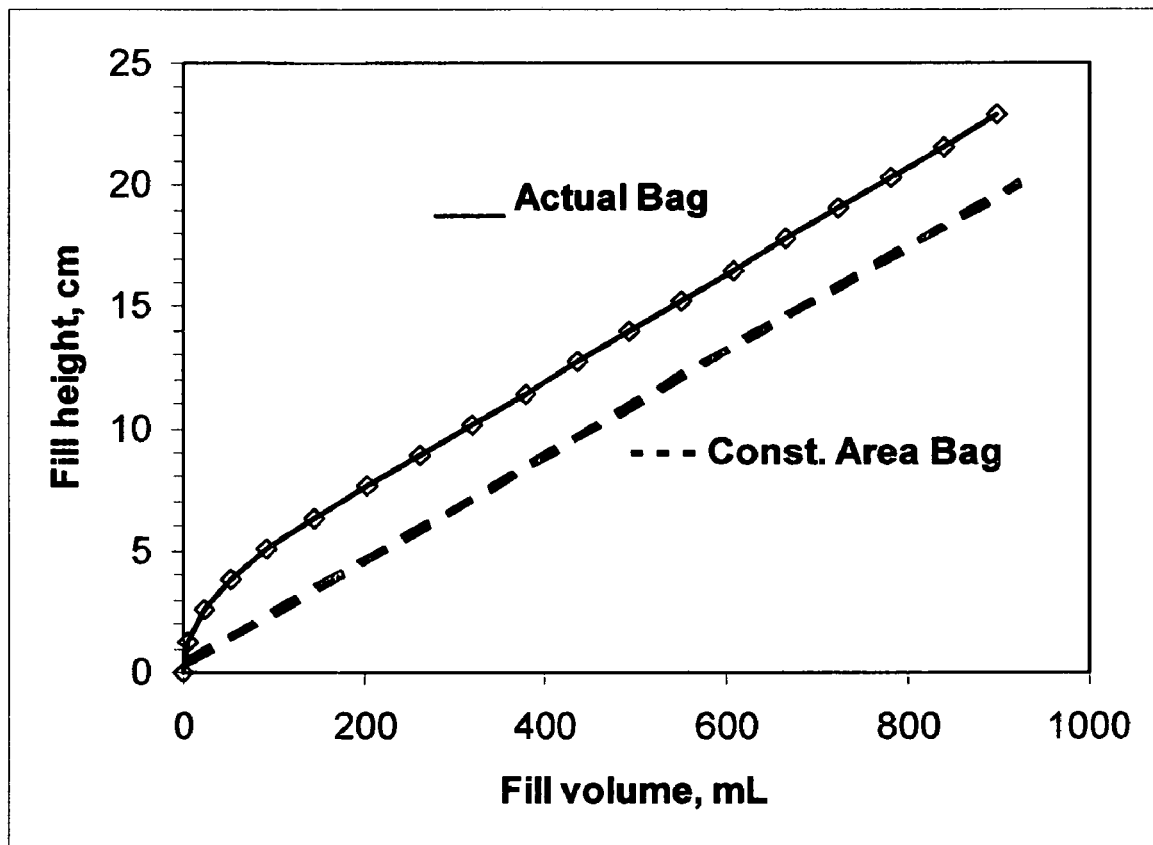
FIG. 24 is a graph of the fill height versus the fill volume for a variable cross-section containment structure and a constant cross-section containment structure.
Figure 26:
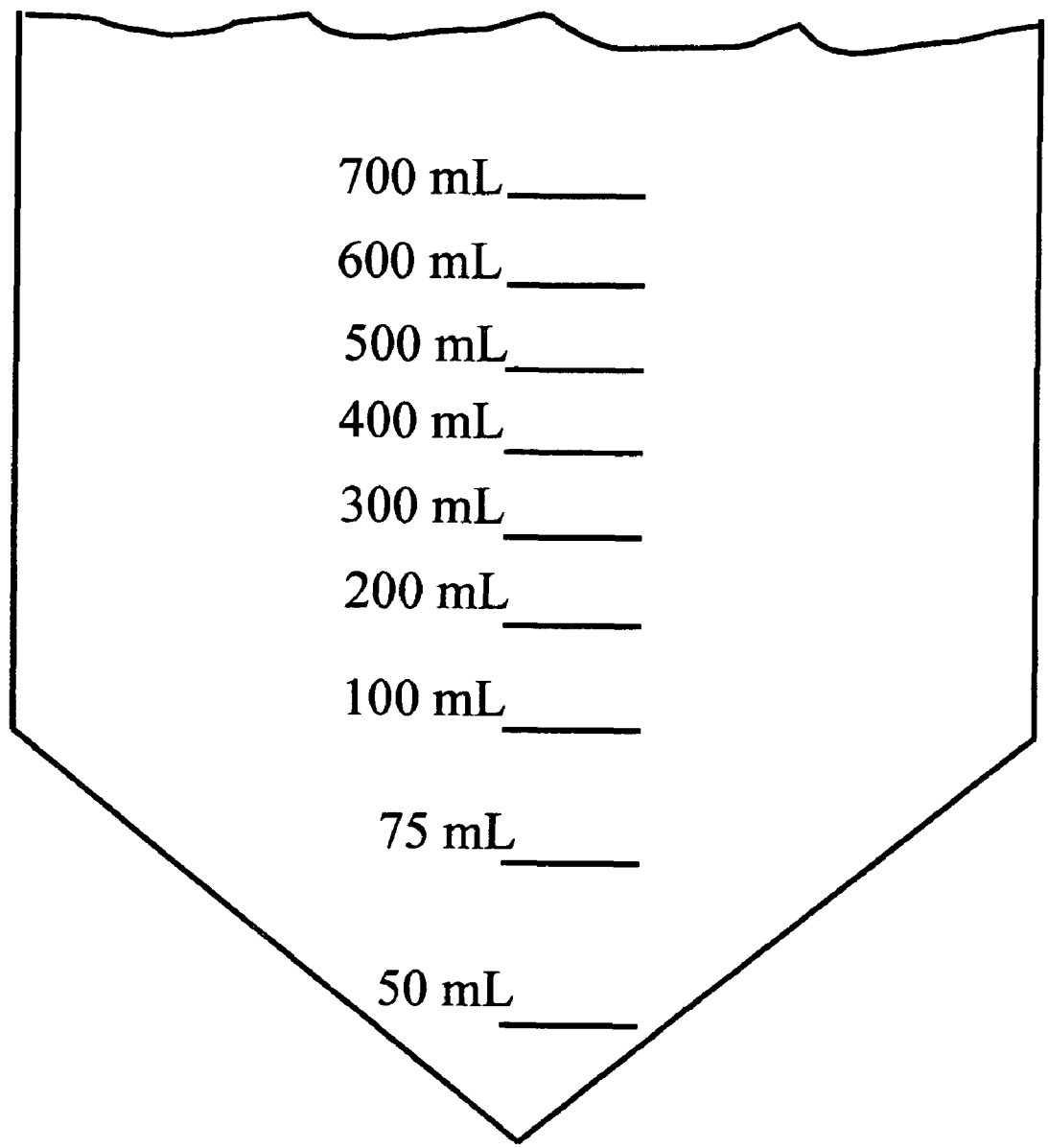
FIG. 26 is a partial side elevation view of a prior art urine collection bag illustrating the irregularly spaced measurement indicia in the variable cross-section portion of the bag.

Now, equations 15 and 16 can be solved for the fluid height (14), designated H in the equations, and plotted, as seen in FIG. 24, for a typical 1000 mL urine collection bag having a width (134, W) of 8.89 cm, a transition length of 6.35 cm, and a convergence angle (144, $\phi$) of 60 degrees. FIG. 24 shows that when the fluid height (14, H) is in the variable cross-section portion (140) of the containment structure (100) the fluid volume varies non-linearly with the fluid height (14, H). One with skill in the art will appreciate that this non-linearity is the reason that the measurement indicia in conventional urine collection bags are non-uniformly spaced in the variable cross-section portion (140), as seen in FIG. 26.

Further, this is the reason that the primary and secondary portions (210, 260) cannot have a constant resistance per unit length of the containment structure length (108), without introducing significant errors when attempting to use a linear signal algorithm. Such non-linear variation of the sensor resistance ($R_{200}$) is graphically illustrated in FIG. 25a. In the variable cross-section portion (140) the fluid height (14, H) is substantially proportional to the square root of the volume, such that:

$$R_{VCS} = R_A - K_A^*(VOL)^{1/2} \quad \text{(equation 17)}$$

where $R_A$ and $K_A$ are constants, and $R_{VCS}$ is the resistance in the variable cross-section portion, thus the VCS subscript. Then, for fluid heights (14, H) in the constant cross-section portion (130) the sensor resistance $R_{200}$ will again vary linearly with volume (VOL).

Figure 25A:
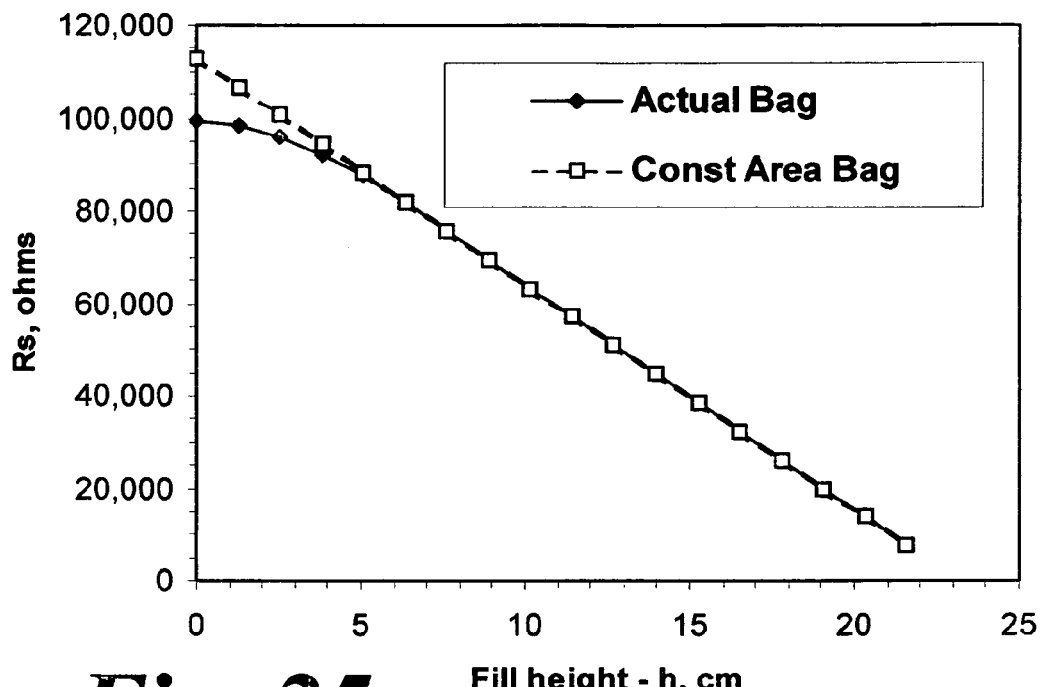
FIG. 25a is a graph of the sensor resistance versus the fill height for a variable cross-section containment structure and a constant cross-section containment structure.
Figure 25B:
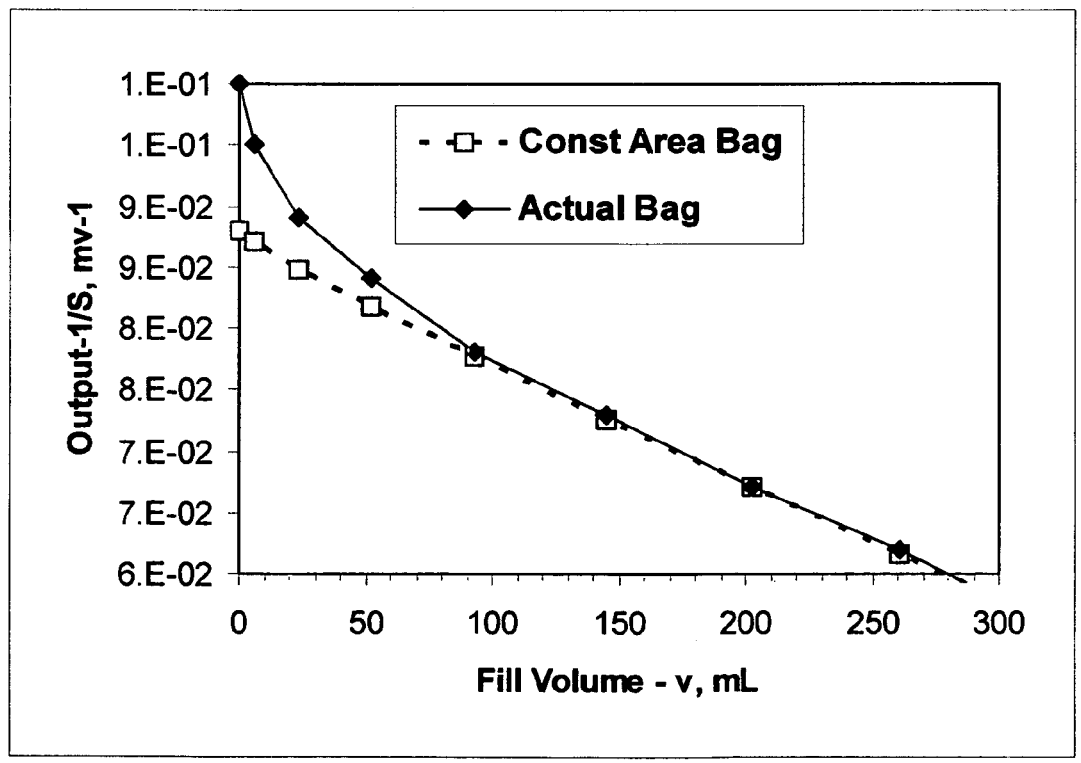
FIG. 25b is a graph of measurement signal versus the fill volume for a variable cross-section containment structure and a constant cross-section containment structure.

Therefore, the measurement signal (202, S) will change in accordance with equation 8 when the fluid height (14, H) is in the constant cross-section portion (130), but when the fluid height (14, H) is in the variable cross-section portion (140) the sensor resistance ($R_{200}$) will change in a non-linear fashion with the fill volume (VOL), as seen in FIG. 25b.

Again, assuming a series circuit with a voltage, S(y), measured across a load resistor (600), the output signal, 1/S(y), as a function of containment structure fill volume (VOL) is given by:

$$1/S(y) = [R_{600} + R_{200}(y)]/(V_{AC}^* R_{600}) \quad \text{(equation 18)}$$

Near the bottom of the containment structure (100), the sensor (200) will change its resistance ($R_{200}$), in a non-linear fashion with fill volume (VOL), as given by equation 17. This can be seen mathematically by substituting equation 17 into equation 18. Thus, in the series circuit embodiment having a load resistor (600) with a resistance ($R_{600}$) that is significantly less than the overall sensor resistance ($R_{200}$), the following measurement signal equation is obtained:

$$1/S(y) = (R_A - K_A^* VOL^2)/(V_{AC}^* R_{600}) \quad \text{(equation 19)}$$

The previously discussed error may be substantially eliminated by varying the resistance of at least a portion of the sensor (200); more specifically, by varying the resistance of at least a portion of the primary portion (210) and a portion of the secondary portion (260) to account for the non-linear effects of the variable cross-section portion (140) of the containment structure (100). Numerous methods of varying the resistance have been previously disclosed herein, and the following analysis focuses on just one of those embodiments, namely the variable width sensor embodiment, however one skilled in the art will understand a similar analysis occurs for the other embodiments. Thus, the primary portion width (218) and the secondary portion width (268) may be varied over a portion of their lengths (216, 266) to account for the non-linear effects of the variable cross-section portion (140) of the containment structure (100). Thus, varying the widths (218, 268) will provide for a measurement signal (202, S(y)) that is more linear than prior constant width and constant resistance per unit length methods, despite the containment structure's varying cross-sectional area. In fact, by varying the sensor's resistance per unit length of the containment structure length (108), in any of the methods disclosed herein, a measurement signal (202, S(y)) may be produced that changes substantially linearly with the amount of fluid (10) in the containment structure (100), despite the containment structure's varying cross-sectional area (142).

Presently focusing on the variable width sensor embodiment, the change in resistance $\Delta R_{200}$ of the sensor (200), for a given change in section length $\Delta L_E$ is given by the following equation:

$$\Delta R_{200} = (R_{SQ})(\Delta L_E/W) \quad \text{(equation 20)}$$

where $R_{SQ}$ is the resistance per square unit, previously explained, for the primary and secondary portions (210, 260) and W is the width of the portions (218, 268). For a constant width, $W = W_C$, the sensor resistance, per unit length, is constant along the portions (210, 260). If, however, the width, W, is changed along the portion length (216, 266, $L_E$), then according to equation 20, $\Delta R_{200}$ will no longer be constant. Therefore, in one embodiment, by adjusting the portion width (W), identified with either element numbers 218, 268, to provide the proper $\Delta R_{200}$ value, the non-linearity in signal 1/S(y) can be converted to a substantially linear change with volume.

We can assume that the sensor resistance $R_{200}$ changes along the portion length (216, 266) as a quadratic function for the section within the variable cross-section portion (140), namely:

$$R_{200(1)} = Ay^2 + By + C \quad \text{(equation 21)}$$

where A, B, and C are constants. We know that for y=0 that $R_{200(1)} = R_{200}$, therefore $C = R_{200}$. We also know that for all y that $$R_{200(2)} = R_{200} - 2(R_{SQ})(y/W) \quad \text{(equation 22)}$$

where W=W(y) is the width of the portions (210, 260) that can vary as a function of the portion wetted length, y, along the entire portion length (216, 266), from y=0 to y=portion length.

Thus, for the constant cross-section portion (130), we can set equation 22 equal to equation 21 to achieve:

$$R_{200} - 2(R_{SQ})(y/W) = Ay^2 + By + R_{200} \quad \text{(equation 23)}$$

Now, solving for W leaves:

$$W = -2(R_{SQ})/(Ay + B) \quad \text{(equation 24)}$$

To determine the constants A and B, we first use the fact that at the portion wetted length of y equal to the transition length (146) of the containment structure (100), that $R_{200(1)}$ from equation 21 must equal the linear resistance value from equation 4a to obtain:

$$A^*(\text{transition length})^2 + B^*(\text{transition length}) + R_{200} = R_E - K^*(\text{transition length}) \quad \text{(equation 25)}$$

Now, solving for A:

$$A = (R_E - R_{200} - K^*(\text{transition length}) - B(\text{transition length}))/(\text{transition length})^2 \quad \text{(equation 26)}$$

Additionally, the slope of the resistance as a function of y must also be equal at y=(transition length), therefore taking the derivative of equation 21 and setting it equal to the derivative of equation 4a we get:

$$2A(\text{transition length})+B=-K \quad \text{(equation 27)}$$

Solving equation 27 for B yields:

$$B=-(K+2*A*(\text{transition length})) \quad \text{(equation 28)}$$

Now, substituting B from equation 28 back into A from equation 26 we get:

$$A=(R_{200}-R_E)/(\text{transition length})^2 \quad \text{(equation 29)}$$

To solve for $R_{200}$, we use equation 18 and assume that $R_{200} \gg R_{600}$, to obtain $$1/S(y)=R_{200}(y)/(V_{AC}*R_{600})$$

Then, solving equation 30 for $R_{200}(y)$ yields:

$$R_{200}(y)=V_{AC}*R_{600}*1/S(y) \quad \text{(equation 31)}$$

And for y=0, $R_{200}=R_{200(i)}$, thus:

$$R_{200(i)}=V_{AC}*R_{600}*1/S(0) \quad \text{(equation 32)}$$

Further, we know that:

$$1/S(y)=SLOPE_1*y+INTERCEPT_1 \quad \text{(equation 33)}$$

Therefore, for y=0 we also get VOL=0, so equation 33 becomes:

$$1/S(0)=INTERCEPT_1 \quad \text{(equation 34)}$$

Substituting equation 34 into equation 32 we get:

$$R_{200(i)}=V_{AC}*R_{600}*INTERCEPT_1 \quad \text{(equation 35)}$$

Where $INTERCEPT_1$ is the signal (1/S) value at VOL=0. A typical sensor produced to date, the $SLOPE_1=-9.48\times10^{-5}$ mV$^{-1}$·mL$^{-1}$, and $INTERCEPT_1=8.64\times10^{-2}$ mV$^{-1}$. Further, for a typical electronic setup $V_{AC}=11.3\times10^3$ mV, and $R_{600}=100$ ohms. Therefore, $R_{200(i)}=97,630$ ohms.

Therefore, if we assume that the sections (210, 260) essentially extend all the way to the containment structure distal end (102), then the portion wetted length, y, is the same as the fluid height (14), and we can summarize the above series of equations. For fluid heights (14) in the variable cross-section portion (140):

$$R_{200}(y)=R_{200(i)}-2*R_{SQ}*(y/W) \quad \text{(equation 36)}$$

$$W=-2*R_{SQ}/(Ay+B) \quad \text{(equation 37)}$$

$$A=(R_{200(i)}-R_E)/(\text{transition length})^2 \quad \text{(equation 38)}$$

$$B=-(K+2*A*(\text{transition length})) \quad \text{(equation 39)}$$

Thus, typical values of $R_{SQ}=300$ ohms, $R_{200(i)}=97,630$ ohms, $R_E=112,900$ ohms, transition length=6.35 cm, and K=4877 ohms/cm, yield A=−378.7 ohms/cm² and B=−67.51 ohms/cm. Then, similarly for fluid heights (14) in the constant cross-section portion (130):

$$R_{200}(y)=R_{200(i)}-2*R_{SQ}*(y/W) \quad \text{(equation 40)}$$

$$W=W_0=0.1524 \text{ cm} \quad \text{(equation 41)}$$

Figure 27:
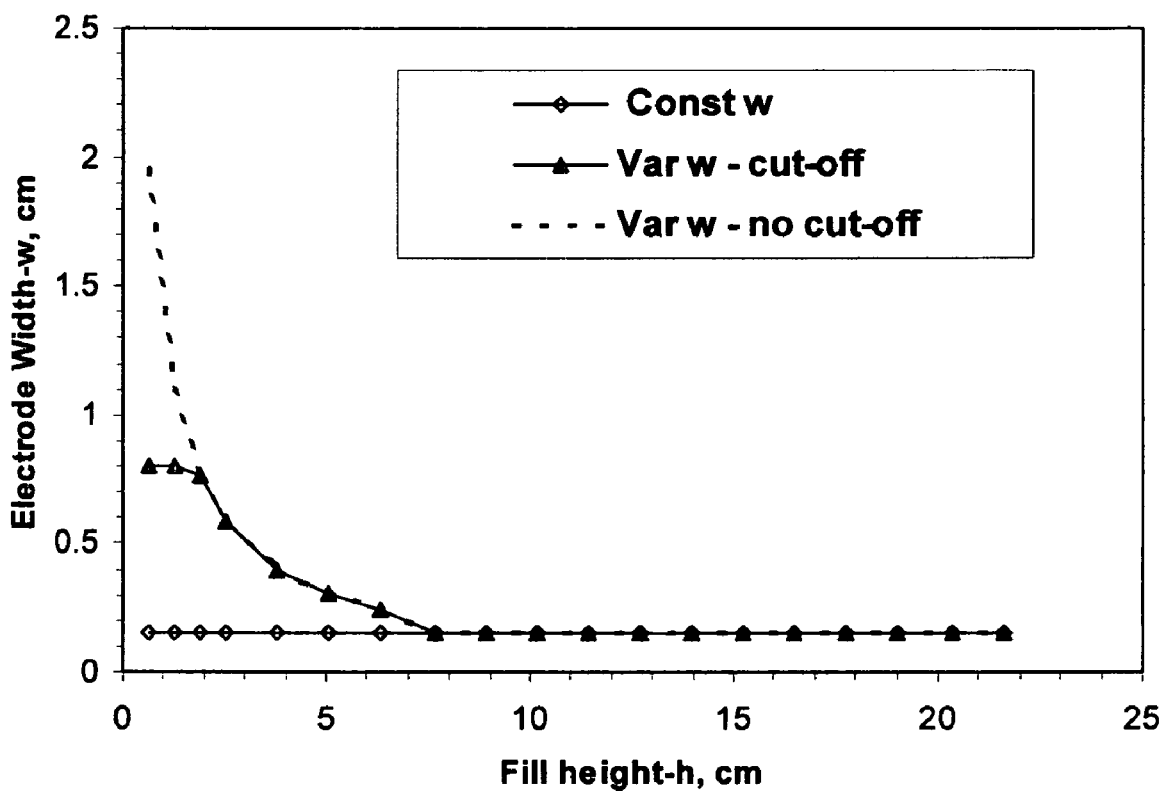
FIG. 27 is a graph of the sensor portion width versus the fill height of one embodiment.
Figure 28:
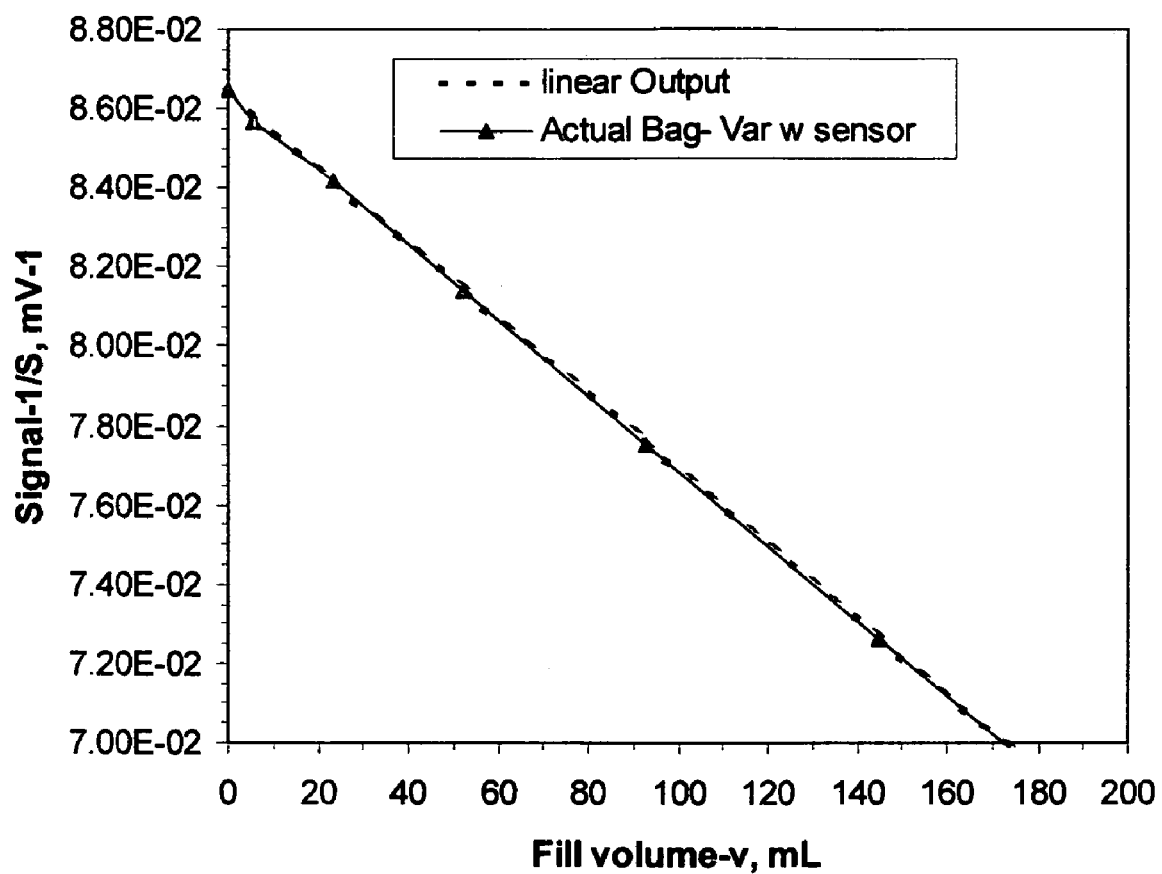
FIG. 28 is a graph of the signal versus the fill volume of one embodiment.
Figure 29:
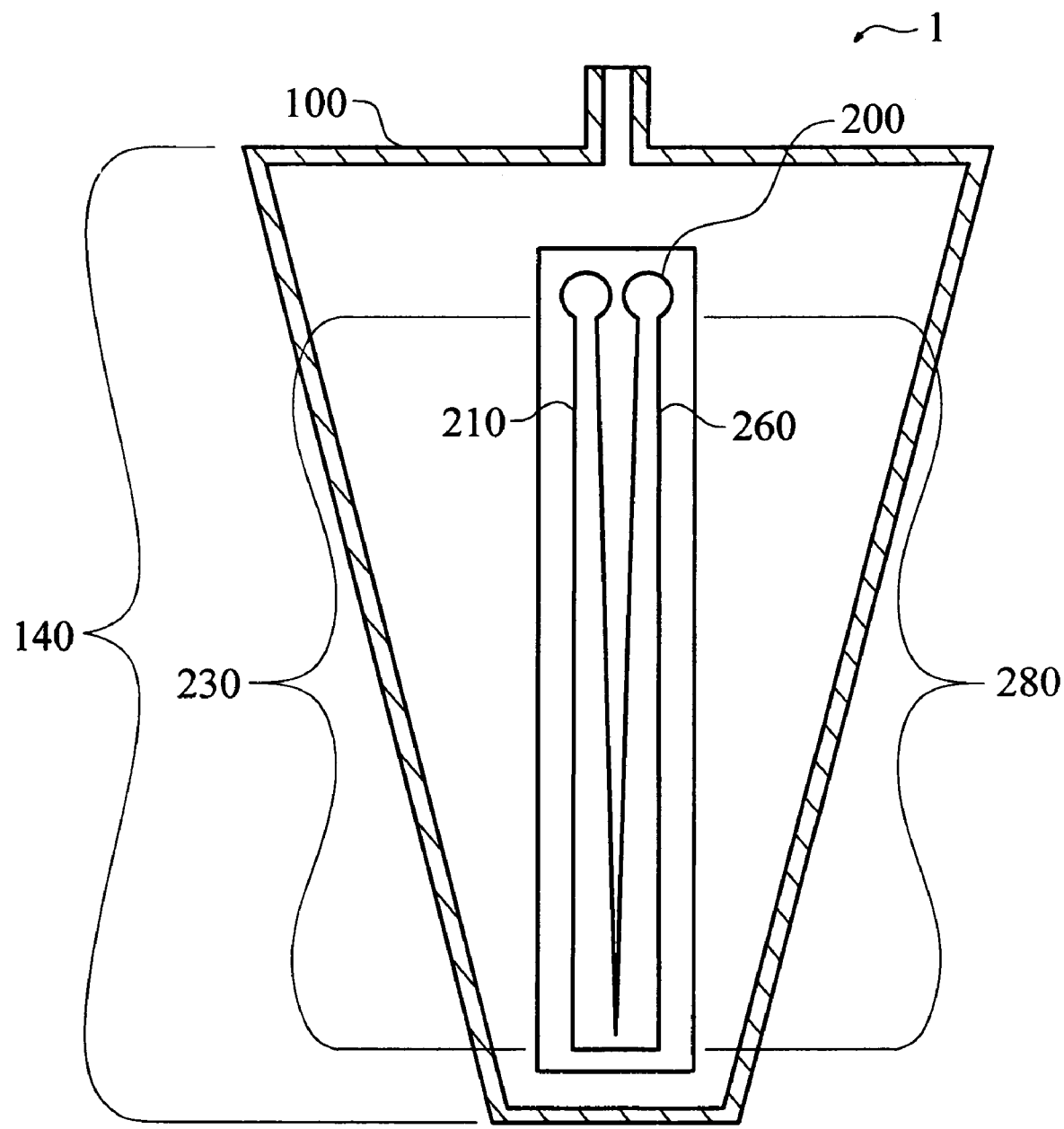
FIG. 29 is a cross-section view of a single variable cross-section portion embodiment of the present invention, not to scale.

Using equation 37, given the parameters above, results in a portion width, W, as a function of fluid height, as shown in FIG. 27. Note, however, that as y approaches zero, the calculated width, W, approaches infinity, indicated by the dashed line labeled in the legend as "Var w-no cut-off" which stands for variable portion width with no predetermined maximum width. Also in FIG. 27 is "Const w" for a constant resistance per unit length sensor, and "Var w-cut-off" for a variable portion width having a maximum width of 0.8 cm. It was determined by calculation that for a fluid height less than 1.27 cm a width cut-off value of 0.8 cm resulted in the desired substantially linear sensor output versus volume characteristic for this particular embodiment, as shown in FIG. 28. Note in FIG. 28 that the accuracy comparison of actual and linear output is made in the most critical area of the volume measurement region (i.e., volume less than 100 mL). These results indicate that using a portion variable resistance section (230, 280) can provide accurate volume measurements for containment structures (100), including actual commercial urine collection bags that have a variable cross-sectional portion.

It is important to note here, that in light of the example above having a width cut-off value, that the term "portion variable resistance section," as used in relation to the primary portion variable resistance section (230) and the secondary portion variable resistance section (280), does not mean that the resistance of the sections, and thus the section widths (218, 268), section thicknesses (219, 269), amount of sensor (200) per unit length of the containment structure length (108), or sensor composition needs to constantly vary over the entire primary portion variable resistance section length (232) and the secondary portion variable resistance section length (282), only that the resistance of the variable resistance sections (230, 280) per unit length of the containment structure length (108) are not constant over the entire lengths (232, 282).

Referring again to FIG. 27 and focusing on the "Var w-cut-off" line, the figure is a plot of the portion width (218, 268) of the previously described embodiment, having a width cut-off value, as a function of portion wetted length, labeled as fill height (h) in the figure. Note that the width of both portions starts at the cut-off value, of 0.8 cm and remains at this cut-off value until h=1.27 cm. The width then decreases in a quadratic fashion with increasing h until it reaches a constant value of $W_{CO}=0.1524$ cm near the transition length of 6.35 cm. The configurations of the portions (210, 260, 290) of this embodiment are illustrated in FIG. 19.

To account for changes in the cross-sectional area at the top of the bag, the width of the portions (210, 260) would again need to increase. This situation will not be described in detail as one with skill in the art will understand that the previous disclosure applies equally as well to the variable cross-section portion (140) near the proximal end (104) of the containment structure (100), and that the same principles regarding the width of the portions (210, 260) at the end nearest the shunt portion (290) may be equally applied to the opposite end of the primary and secondary portions (210, 260). When this invention is applied to the medical field, namely to urine collection bags, it is not that important to maintain accuracy in the upper-bag region because the bag is over 80% full at this point and needs to be emptied.

Now that the physics of the sensor (200) operation has been disclosed, additional embodiments must be discussed. As previously explained, the variable resistance sections (230, 280) are generally substantially located in the variable cross-section portion (140) of the containment structure (100). Thus, in this embodiment, seen in FIG. 1, the primary portion constant resistance section (220) is located substantially within the constant cross-section portion (130) of the containment structure (100), the primary portion variable resistance section (230) is substantially located within the variable cross-section portion (140) of the containment structure (100), secondary portion constant resistance section (260) is located within the constant cross-section portion (130) of the containment structure (100), and the secondary portion variable resistance section (280) is located within the variable cross-section portion (140) of the containment structure (100). This embodiment allows the portion variable width sections (230, 280) to be located substantially in the variable cross-section portion (140) thereby allowing the portion's resistance to vary in only that portion of the containment structure (100) having a variable cross-section (142). In fact, the location of the transition from the primary portion constant resistance section (220) to the primary portion variable resistance section (230) generally corresponds to the transition from the containment structure's constant cross-section portion (130) to the variable cross-section portion (140), and similarly for the secondary portion (260). The distance of this transition from the containment structure distal end (102) is known as the transition length (146).

In fact, in yet another embodiment, referring again to FIG. 4, the primary portion width (218) increases, from the primary portion initiation width (234) to the primary portion termination width (236), as the variable cross-section (142) decreases. Similarly, the secondary portion width (268) increases, from the secondary portion initiation width (284) to the secondary portion termination width (286), as the variable cross-section (142) decreases. Such an increase in the widths (218, 268) allows the measurement signal (202) to more linearly track the volume of fluid (10) in the containment structure (100), as previously explained. Again, it should be noted that the increase in the widths (218, 268), like the change in the sensor resistance per unit length of the containment structure length (108), need not be constant, or continuous, however certain embodiments have particular patterns to the increase in widths (218, 268), or resistance per unit length. In fact, it is common, in the many embodiments disclosed herein, for the widths (218, 268) to increase continuously from the section initiation widths (234, 284) to the section termination widths (236, 286), and then remain constant over the remainder of the section lengths (216, 266), as seen in FIG. 19.

In still a further embodiment, the changes in resistance per unit length are selected such that a predetermined characteristic of the electrical measurement signal (202) changes substantially linearly with changes in the fluid height in the variable cross-section portion (140). One with skill in the art will recognize that the predetermined characteristics of the measurement signal (202) may include changes in voltage as well as current, and other electrical characteristics.

While the primary portion (210) and the secondary portion (260) need not be identical, in one embodiment the primary portion variable width section (230) is identical to the secondary portion variable width section (280), as seen in FIG. 4. Further, the primary portion width (218) from the primary portion initiation width (234) to the primary portion termination width (236) may be substantially the same as the secondary portion width (268) from the secondary portion initiation width (284) to the secondary portion termination width (286). Likewise, the primary portion thickness (219) may be substantially the same as the secondary portion thickness (269), as seen in FIGS. 5 and 6. Similarly, the changes in the primary portion's (210) resistance per unit length of the containment structure length (108), i.e. the pattern in which the primary portion (210) traverses the containment structure length (108), may be substantially the same as the changes in the secondary portion's (260) resistance per unit length of the containment structure length (108), as seen in FIG. 10. Such embodiments incorporating primary and secondary portions (210, 260) that are substantially mirror images of each other increase the ease in which the invention is manufactured and improves the predictability of the inventions performance.

In yet a further embodiment seeking to obtain a desirable substantially linear relationship between changes in the fluid volume and changes in the measurement signal, the primary portion width (218) increases in a substantially quadratic fashion from the primary portion initiation width (234), and the secondary portion width (268) increases in a substantially quadratic fashion from the secondary portion initiation width (284), as seen in FIGS. 7 and 19. Such quadratic expansion of the width of the primary and secondary portions (210, 260) may occur on one longitudinal edge of the sections (210, 260), as seen in FIGS. 7 and 19, or it may occur on both longitudinal edges such that the section "bells" out near the distal ends (212, 262), as seen in FIG. 20.

Now, with regard to the placement of the sensor (200), it may be integral to the containment structure (100), or it may be a separate entity mounted within the containment structure (100). For instance, in one embodiment the portions (210, 260) are printed directly on the containment wall interior surface (124). In another embodiment the portions (210, 260) are formed in, or with, the containment structure (100). Alternatively, in another embodiment the sensor (200) may include a sensor substrate (204) to which the primary portion (210) and the secondary portion (260) are mounted, as seen in FIG. 4. The sensor substrate (204) may then be positioned within the containment structure (100), or the sensor substrate (204) may be joined to the containment structure (100) during the manufacturing process, as would be the case of the embodiment of FIG. 18. In any of these embodiments, the portions (210, 260) may be formed of conductive ink that is printed on the containment structure (100), or the substrate (204). Such printing techniques make it easy to change the sensors' widths (218, 268), thicknesses (219, 269), and patterns of the portions (210, 260) as they traverse the containment structure (100). For instance, multiple passes of the printing device may be used to change the thickness profile of the primary and secondary portions (210, 260). In one particular embodiment, the conductive ink is a carbon ink.

In a further embodiment, the portions (210, 260) are selected to have a high resistance relative to that of the fluid (10). In this particular embodiment the electrical resistance of the primary portion (210) and the secondary portion (260) is greater than approximately 1000 ohms per centimeter. The containment structure (100) may be a rigid structure or it may be a pliable structure. In most medical applications, the containment structure (100) will be a pliable structure constructed of a pliable material such as sheets of vinyl material joined using radio-frequency (RF) welding techniques. However, it should be noted that the containment structure (100) may be constructed of virtually any liquid-tight material. Further, the containment structure (100) is not required to have a constant cross-section portion (130), rather that is simply how most containment structures in the medical industry are made. For instance, the containment structure (100) may only have a single variable cross-section portion (140), such as a the inverted pyramid shape of FIG. 29, or may incorporate multiple variable cross-section portions (140), as seen in FIG. 30. Thus, one with skill in the art will recognize that the prior disclosure covers such embodiments and that the sensor (200) of such embodiments need only have a primary portion variable resistance section (230) and a secondary portion variable resistance section (280), and need not have the primary and secondary constant resistance sections (220, 270).

The present invention may be used to measure any electrically conductive fluid. It is particularly suited to measure low resistance fluids including most physiological fluids such as electrolyte solution in IV bags or urine, and blood. The term "electrical resistance," or "resistance," used herein means the resistance of a material to electron or ion flow. Use of the term "portions (210, 260)" herein is meant to include the shunt portion (290) in the embodiments that include a shunt portion (290). Further, the equations, calculations, and examples described herein are not intended to limit the invention in any way and are merely disclosures of one of many particular embodiments of the present invention.

One with skill in the art will recognize that the primary and secondary portions (210, 260) of the sensor (200) of the present invention may traverse the containment structure (100) in any manner and orientation. Thus, although the primary and secondary portions (210, 260) are generally shown as beginning near the containment structure proximal end (104) and ending near the distal end (102), the portions are not limited to this configuration. Further, although the figures always show the primary and secondary portions (210, 260) on the same containment wall surface, this is not required and one skilled in the art will recognize that in one embodiment the primary portion (210) may be on the opposite wall as the secondary portion (260) with the portions (210) connected at the containment structure distal end (102).

The variable cross-section containment structure liquid measurement device (1) is useful in continuously measuring the amount of fluid in any containment structure, whether the fluid is being collected in the structure, for example, as in urine collection bags, or being dispensed from the structure, for example, as in intravenous delivery bags.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims.

INDUSTRIAL APPLICABILITY

A liquid measurement device having a containment structure, a sensor, and an interface device, having particular applicability to the collection and administration of electrically conductive fluids. The device is configured to house and continuously monitor the height of a fluid in the containment structure. The containment structure has at least one variable cross-section portion. The sensor has two cooperating variable resistance sections that account for the variable cross-section of the containment structure. The electrical resistance of the sensor changes as the fluid height changes and shorts out a portion of the sensor. The sensor may include an electrically conductive ink that is printed on the interior of the containment structure. The sensor receives an electrical measurement signal and modifies the signal in a predetermined manner to reflect the amount of fluid within the containment structure. The device is useful in continuously measuring the amount of fluid in urine collection bags and intravenous bags. The interface device may display the measurement information or transmit it to other equipment.

I claim:

1. A variable cross-section containment structure liquid measurement device (1) for housing a fluid (10) and monitoring a fluid height (14) of a surface (12) of the fluid (10), wherein the liquid measurement device (1) is in fluid communication with an external fluid channel (500), comprising:
A) a containment structure (100), having an interior (106), for housing the fluid (10), having,
  (i) a distal end (102);
  (ii) a proximal end (104) separated from the distal end (102) by a containment structure length (108);
  (iii) at least one containment wall (120), joining the containment structure distal end (102) and the containment structure proximal end (104), having a wall thickness (122), an interior surface (124), and an exterior surface (126), wherein the containment wall (120) defines a maximum containment volume sealed from the exterior environment;
  (iv) a port (110) attached to the containment wall (120) and configured to releasably connect to the external fluid channel (500) thereby permitting fluid communication between the containment structure interior (106) and the exterior fluid channel (500);
  (v) a constant cross-section portion (130) having a constant cross-section (132);
  (vi) a variable cross-section portion (140) formed by a convergence of the containment wall (120) at a convergence angle (144), and having a variable cross-section (142) and a transition length (146);
B) a sensor (200) located within the containment structure interior (106) that modifies an electrical measurement signal (202) in a predetermined manner to reflect the amount of fluid (10) within the containment structure (10), having,
  (i) a primary portion (210) having,
    (a) a primary portion distal end (212),
    (b) a primary portion proximal end (214),
    (c) a primary portion length (216),
    (d) a primary portion width (218),
    (e) a primary portion thickness (219),
    (f) a primary portion constant resistance section (220) having a primary portion constant resistance section length (222), wherein the electrical resistance of the primary portion constant resistance section (220) per unit length of the containment structure length (108) is substantially constant, and
    (g) a primary portion variable resistance section (230) having a primary portion variable resistance section length (232), wherein the electrical resistance of the primary portion variable resistance section (230) per unit length of the containment structure length (108) varies over at least a portion of the primary portion variable resistance section (230) when the primary portion variable resistance section (230) is outside the fluid;
  (ii) a secondary portion (260), in electrical communication with the primary portion (210) when the primary portion (210) and secondary portion (260) are outside the fluid, having,
    (a) a secondary portion distal end (262),
    (b) a secondary portion proximal end (264),
    (c) a secondary portion length (266),
    (d) a secondary portion width (268),
    (e) a secondary portion thickness (269),
    (f) a secondary portion constant resistance section (270) having a secondary portion constant resistance section length (272), wherein the electrical resistance of the secondary portion constant resistance section (270) per unit length of the containment structure length (108) is substantially constant, and
(g) a secondary portion variable resistance section (280) having a secondary portion variable resistance section length (282), wherein the electrical resistance of the secondary portion variable resistance section (280) per unit length of the containment structure length (108) varies over at least a portion of the secondary portion variable resistance section (280) when the secondary variable resistance section (280) is outside the fluid; and C) an interface device (300) having an interior interface portion (310) located substantially in the containment structure interior (106), and an exterior interface portion (320) located substantially external to the containment structure (100), wherein the interior interface portion (310) is connected to a portion of the primary portion (210) and a portion of the secondary portion (260), and wherein the measurement signal (202) is transmitted between the interior interface portion (310) and the exterior interface portion (320).

2. The variable cross-section containment structure liquid measurement device (1) of claim 1, wherein the primary portion constant resistance section (220) is located substantially within the constant cross-section portion (130) of the containment structure (100), the primary portion variable resistance section (230) is located substantially within the variable cross-section portion (140) of the containment structure (100), secondary portion constant resistance section (260) is located substantially within the constant cross-section portion (130) of the containment structure (100), and the secondary portion variable resistance section (280) is located substantially within the variable cross-section portion (140) of the containment structure (100).

3. The variable cross-section containment structure liquid measurement device (1) of claim 2, wherein the primary portion width (218) and the primary portion thickness (219) are substantially constant over the primary portion constant resistance section length (222), and the secondary portion width (268) and the secondary portion thickness (269) are substantially constant over the secondary portion constant resistance section length (272).

4. The variable cross-section containment structure liquid measurement device (1) of claim 2, wherein the primary portion width (218) varies over at least a portion of the primary portion variable resistance section (230), and the secondary portion width (268) varies over at least a portion of the secondary portion variable resistance section (280).

5. The variable cross-section containment structure liquid measurement device (1) of claim 4, wherein the primary portion width (218) increases, from a primary portion initiation width (234) to a primary portion termination width (236), as the variable cross-section (142) decreases, and the secondary portion width (268) increases, from a secondary portion initiation width (284) to a secondary portion termination width (286), as the variable cross-section (142) decreases.

6. The variable cross-section containment structure liquid measurement device (1) of claim 5, wherein the primary portion width (218) from the primary portion initiation width (234) to the primary portion termination width (236) is substantially the same as the secondary portion width (268) from the secondary portion initiation width (284) to the secondary portion termination width (286).

7. The variable cross-section containment structure liquid measurement device (1) of claim 5, wherein the primary portion width (218) increases m a substantially quadratic fashion from the primary portion initiation width (234) to the primary portion termination width (236), and the secondary portion width (268) increases in a substantially quadratic fashion from the secondary portion initiation width (284) to the secondary portion termination width (286).

8. The variable cross-section containment structure liquid measurement device (1) of claim 1, wherein a predetermined characteristic of the electrical measurement signal (202) changes substantially linearly with changes in the fluid height in the variable cross-section portion (140).

9. The variable cross-section containment structure liquid measurement device (1) of claim 1, wherein the primary portion thickness (219) varies over at least a portion of the primary portion variable resistance section (230), and the secondary portion thickness (269) varies over at least a portion of the secondary portion variable resistance section (280).

10. The variable cross-section containment structure liquid measurement device (1) of claim 1, wherein the sensor (200) further includes a shunt portion (290) connecting the primary portion distal end (212) to the secondary portion distal end (262).

11. The variable cross-section containment structure liquid measurement device (1) of claim 1, wherein the electrical resistance of the primary portion (210) and the secondary portion (260) is greater than 1000 ohms per centimeter.

12. The variable cross-section containment structure liquid measurement device (1) of claim 1, wherein the primary portion (210) and the secondary portion (260) are formed of conductive ink.

13. The variable cross-section containment structure liquid measurement device (1) of claim 12, wherein the primary portion (210) and the secondary portion (260) are printed on the containment wall interior surface (124).

14. The variable cross-section containment structure liquid measurement device (1) of claim 1, wherein the containment structure (100) is constructed of a pliable material.

15. The variable cross-section containment structure liquid measurement device (1) of claim 1, further including a data acquisition device (400) in electrical communication with the interface device (300), wherein the data acquisition device (400) generates the measurement signal (202) and analyzes changes in the measurement signal (202).

16. The variable cross-section containment structure liquid measurement device (1) of claim 15, wherein the containment structure (100) further includes an auxiliary mounting pocket (150) to releasably house the data acquisition device (400).

17. The variable cross-section containment structure liquid measurement device (1) of claim 15, wherein the data acquisition device (400) includes a wireless transmitter (410).

18. The variable cross-section containment structure liquid measurement device (1) of claim 1, wherein the interior interface portion (310) and the exterior interface portion (320) are capacitively coupled across the containment wall (120) to transmit the measurement signal (202).

19. A variable cross-section containment structure liquid measurement device (1) for housing a fluid (10) and monitoring a fluid height (14) of a surface (12) of the fluid (10), wherein the liquid measurement device (1) is in fluid communication with an external fluid channel (500), comprising:
A) a containment structure (100), having an interior (106), for housing the fluid (10), having,
(i) a distal end (102);
(ii) a proximal end (104) separated from the distal end (102) by a containment structure length (108);
(iii) at least one containment wall (120), joining the containment structure distal end (102) and the containment structure proximal end (104), having a wall thickness (122), an interior surface (124), and an exterior surface (126), wherein the containment wall (120) defines a maximum containment volume sealed from the exterior environment;
(iv) a port (110) attached to the containment wall (120) and configured to releasably connect to the external fluid channel (500) thereby permitting fluid communication between the containment structure interior (106) and the exterior fluid channel (500);
(v) a constant cross-section portion (130) having a constant cross-section (132);
(vi) a variable cross-section portion (140) formed by a convergence of the containment wall (120) at a convergence angle (144), and having a variable cross-section (142) and a transition length (146);

B) a sensor (200) located within the containment structure interior (106) that modifies an electrical measurement signal (202) in a predetermined manner to reflect the amount of fluid (10) within the containment structure (10), having,
(i) a primary portion (210) having,
(a) a primary portion distal end (212),
(b) a primary portion proximal end (214),
(c) a primary portion length (216),
(d) a primary portion width (218),
(e) a primary portion thickness (219),
(f) a primary portion constant resistance section (220), located substantially within the constant cross-section portion (130) of the containment structure (100), having a primary portion constant resistance section length (222), wherein the electrical resistance of the primary portion constant resistance section (220) per unit length of the containment structure length (108) is substantially constant, and
(g) a primary portion variable resistance section (230), located substantially within the variable cross-section portion (140) of the containment structure (100), having a primary portion variable resistance section length (232), wherein the electrical resistance of the primary portion variable resistance section (230) per unit length of the containment structure length (108) varies over at least a portion of the primary portion variable resistance section (230) when the primary portion variable resistance section (230) is outside the fluid;
(ii) a secondary portion (260), in electrical communication with the primary portion (210) when the primary portion (210) and the secondary portion (260) are outside the fluid, having,
(a) a secondary portion distal end (262),
(b) a secondary portion proximal end (264),
(c) a secondary portion length (266),
(d) a secondary portion width (268),
(e) a secondary portion thickness (269),
(f) a secondary portion constant resistance section (270), located substantially within the constant cross-section portion (130) of the containment structure (100), having a secondary portion constant resistance section length (272), wherein the electrical resistance of the secondary portion constant resistance section (270) per unit length of the containment structure length (108) is substantially constant, and
(g) a secondary portion variable resistance section (280), located substantially within the variable cross-section portion (140) of the containment structure (100), having a secondary portion variable resistance section length (282), wherein the electrical resistance of the secondary portion variable resistance section (280) per unit length of the containment structure length (108) varies over at least a portion of the secondary portion variable resistance section (280) when the secondary portion variable resistance section (280) is outside the fluid; and
C) an interlace device (300) having an interior interface portion (310) located substantially in the containment structure interior (106), and an exterior interface portion (320) located substantially external to the containment structure (100), wherein the interior interface portion (310) is connected to a portion of the primary portion (210) and a portion of the secondary portion (260), and wherein the measurement signal (202) is transmitted between the interior interface portion (310) and the exterior interface portion (320).

20. The variable cross-section containment structure liquid measurement device (1) of claim 19, wherein the primary portion width (218) and the primary portion thickness (219) are substantially constant over the primary portion constant resistance section length (222), and the secondary portion width (268) and the secondary portion thickness (269) are substantially constant over the secondary portion constant resistance section length (272).

21. The variable cross-section containment structure liquid measurement device (1) of claim 19, wherein the primary portion width (218) varies over at least a portion of the primary portion variable resistance section (230), and the secondary portion width (268) varies over at least a portion of the secondary portion variable resistance section (280).

22. The variable cross-section containment structure liquid measurement device (1) of claim 21, wherein the primary portion width (218) increases, from a primary portion initiation width (234) to a primary portion termination width (236), as the variable cross-section (142) decreases, and the secondary portion width (268) increases, from a secondary portion initiation width (284) to a secondary portion termination width (286), as the variable cross-section (142) decreases.

23. The variable cross-section containment structure liquid measurement device (1) of claim 21, wherein the primary portion width (218) from the primary portion initiation width (234) to the primary portion termination width (236) is substantially the same as the secondary portion width (268) from the secondary portion initiation width (284) to the secondary portion termination width (286).

24. The variable cross-section containment structure liquid measurement device (1) of claim 21, wherein the primary portion width (218) increases in a substantially quadratic fashion from the primary portion initiation width (234) to the primary portion termination width (236), and the secondary portion width (268) increases in a substantially quadratic fashion from the secondary portion initiation width (284) to the secondary portion termination width (286).

25. The variable cross-section containment structure liquid measurement device (1) of claim 19, wherein a predetermined characteristic of the electrical measurement signal (202) changes substantially linearly with changes in the fluid height in the variable cross-section portion (140).

26. The variable cross-section containment structure liquid measurement device (1) of claim 19, wherein the primary portion thickness (219) vanes over at least a portion of the primary portion variable resistance section (230), and the secondary portion thickness (269) varies over at least a portion of the secondary portion variable resistance section (280).

27. A variable cross-section containment structure liquid measurement device (1) for housing a fluid (10) and monitoring a fluid height (14) of a surface (12) of the fluid (10), wherein the liquid measurement device (1) is in fluid communication with an external fluid channel (500), comprising:

A) a containment structure (100), having an interior (106), for housing the fluid (10), having,
  (i) a distal end (102);
  (ii) a proximal end (104) separated from the distal end (102) by a containment structure length (108);
  (iii) at least one containment wall (120), joining the containment structure distal end (102) and the containment structure proximal end (104), having a wall thickness (122), an interior surface (124), and an exterior surface (126), wherein the containment wall (120) defines a maximum containment volume sealed from the exterior environment;
  (iv) a port (110) attached to the containment wall (120) and configured to releasably connect to the external fluid channel (500) thereby permitting fluid communication between the containment structure interior (106) and the exterior fluid channel (500);
  (v) a constant cross-section portion (130) having a constant cross-section (132);
  (vi) a variable cross-section portion (140) formed by a convergence of the containment wall (120) at a convergence angle (144), and having a variable cross-section (142) and a transition length (146);

B) a sensor (200) located within the containment structure interior (106) that modifies an electrical measurement signal (202) in a predetermined manner to reflect the amount of fluid (10) within the containment structure (10), having,
  (i) a primary portion (210) having,
    (a) a primary portion distal end (212),
    (b) a primary portion proximal end (214),
    (c) a primary portion length (216),
    (d) a primary portion width (218),
    (e) a primary portion thickness (219),
    (f) a primary portion constant resistance section (220), located substantially within the constant cross-section portion (130) of the containment structure (100), having a primary portion constant resistance section length (222), wherein the electrical resistance of the primary portion constant resistance section (220) per unit length of the containment structure length (108) is substantially constant, and wherein the primary portion width (218) and the primary portion thickness (219) are substantially constant over the primary portion constant resistance section length (222), and
    (g) a primary portion variable resistance section (230), located substantially within the variable cross-section portion (140) of the containment structure (100), having a primary portion variable resistance section length (232), wherein the electrical resistance of the primary portion variable resistance section (230) per unit length of the containment structure length (108) varies over at least a portion of the primary portion variable resistance section (230) when the primary portion variable resistance section (230) is outside the fluid and the primary portion width (218) increases over at least a portion of the primary portion variable resistance section (230) as the variable cross-section (142) decreases;
  (ii) a secondary portion (260), in electrical communication with the primary portion (210) when the primary portion (210) and the secondary portion (260) are outside the fluid, having,
    (a) a secondary portion distal end (262),
    (b) a secondary portion proximal end (264),
    (c) a secondary portion length (266),
    (d) a secondary portion width (268),
    (e) a secondary portion thickness (269),
    (f) a secondary portion constant resistance section (270), located substantially within the constant cross-section portion (130) of the containment structure (100), having a secondary portion constant resistance section length (272), wherein the electrical resistance of the secondary portion constant resistance section (270) per unit length of the containment structure length (108) is substantially constant, and wherein the secondary portion width (268) and the secondary portion thickness (269) are substantially constant over the secondary portion constant resistance section length (272), and
    (g) a secondary portion variable resistance section (280), located substantially within the variable cross-section portion (140) of the containment structure (100), having a secondary portion variable resistance section length (282), wherein the electrical resistance of the secondary portion variable resistance section (280) per unit length of the containment structure length (108) varies over at least a portion of the secondary portion variable resistance section (280) when the secondary portion variable resistance section (280) is outside the fluid and the secondary portion width (268) increases over at least a portion of the secondary portion variable resistance section (280) as the variable cross-section (142) decreases; and C) an interface device (300) having an interior interface portion (310) located substantially in the containment structure interior (106), and an exterior interface portion (320) located substantially external to the containment structure (100), wherein the interior interface portion (310) is connected to a portion of the primary portion (210) and a portion of the secondary portion (260), and wherein the measurement signal (202) is transmitted between the interior interface portion (310) and the exterior interface portion (320), and wherein a predetermined characteristic of the electrical measurement signal (202) changes substantially linearly with changes in the fluid height in the variable cross-section portion (140).

28. A variable cross-section containment structure liquid measurement device (1) for housing a fluid (10) and monitoring a fluid height (14) of a surface (12) of the fluid (10), wherein the liquid measurement device (1) is in fluid communication with an external fluid channel (500), comprising:

A) a containment structure (100), having an interior (106), for housing the fluid (10), having,
  (i) a distal end (102);
  (ii) a proximal end (104) separated from the distal end (102) by a containment structure length (108);
  (iii) at least one containment wall (120), joining the containment structure distal end (102) and the containment structure proximal end (104), having a wall thickness (122), an interior surface (124), and an exterior surface (126), wherein the containment wall (120) defines a maximum containment volume sealed from the exterior environment;

(iv) a port (110) attached to the containment wall (120) and configured to releasably connect to the external fluid channel (500) thereby permitting fluid communication between the containment structure interior (106) and the exterior fluid channel (500);

(v) a variable cross-section portion (140) formed by a convergence of the containment wall (120) at a convergence angle (144), and having a variable cross-section (142) and a transition length (146);

B) a sensor (200) located within the containment structure interior (106) that modifies an electrical measurement signal (202) in a predetermined manner to reflect the amount of fluid (10) within the containment structure (10), having, (i) a primary portion (210) having,
(a) a primary portion distal end (212),
(b) a primary portion proximal end (214),
(c) a primary portion length (216),
(d) a primary portion width (218),
(e) a primary portion thickness (219), and
(f) a primary portion variable resistance section (230) having a primary portion variable resistance section length (232), wherein the electrical resistance of the primary portion variable resistance section (230) per unit length of the containment structure length (108) varies over at least a portion of the primary portion variable resistance section (230) when the primary portion variable resistance section (230) is outside the fluid;

(ii) a secondary portion (260), in electrical communication with the primary portion (210) when the primary portion (210) and the secondary portion (260) is outside the fluid, having,
(a) a secondary portion distal end (262),
(b) a secondary portion proximal end (264),
(c) a secondary portion length (266),
(d) a secondary portion width (268),
(e) a secondary portion thickness (269), and
(f) a secondary portion variable resistance section (280) having a secondary portion variable resistance section length (282), wherein the electrical resistance of the secondary portion variable resistance section (280) per unit length of the containment structure length (108) varies over at least a portion of the secondary portion variable resistance section (280) when the secondary portion variable resistance section (280) is outside the fluid; and C) an interface device (300) having an interior interface portion (310) located substantially in the containment structure interior (106), and an exterior interface portion (320) located substantially external to the containment structure (100), wherein the interior interface portion (310) is connected to a portion of the primary portion (210) and a portion of the secondary portion (260), and wherein the measurement signal (202) is transmitted between the interior interface portion (310) and the exterior interface portion (320).

29. The variable cross-section containment structure liquid measurement device (1) of claim 28, wherein the primary portion width (218) varies over at least a portion of the primary portion variable resistance section (230), and the secondary portion width (268) varies over at least a portion of the secondary portion variable resistance section (280).

30. The variable cross-section containment structure liquid measurement device (1) of claim 29, wherein the primary portion width (218) increases, from a primary portion initiation width (234) to a primary portion termination width (236), as the variable cross-section (142) decreases, and the secondary portion width (268) increases, from a secondary portion initiation width (284) to a secondary portion termination width (286), as the variable cross-section (142) decreases.

31. The variable cross-section containment structure liquid measurement device (1) of claim 30, wherein the primary portion width (218) increases in a substantially quadratic fashion from the primary portion initiation width (234) to the primary portion termination width (236), and the secondary portion width (268) increases in a substantially quadratic fashion from the secondary portion initiation width (284) to the secondary portion termination width (286).

32. The variable cross-section containment structure liquid measurement device (1) of claim 28, wherein a predetermined characteristic of the electrical measurement signal (202) changes substantially linearly with changes in the fluid height in the variable cross-section portion (140).

33. A liquid measurement device (1) for housing a fluid (10) and monitoring a fluid height (14) of a surface (12) of the fluid (10), comprising:

A) a containment structure (100), having an interior (106), for housing the fluid (10), having,
(i) a distal end (102); and
(ii) a proximal end (104) separated from the distal end (102) by a containment structure length (108); and B) a sensor (200) located within the containment structure interior (106) that modifies an electrical measurement signal (202) in a predetermined manner to reflect the amount of fluid (10) within the containment structure, having,
(i) a vertical primary portion (210) extending along the length of the containment structure (100) between the distal end (102) and the proximal end (104) of the containment structure (100) with a total resistance R(210), the vertical primary portion (210) having a distal end (212) and a proximal end (214):
(ii) a vertical secondary portion (260) extending along the length of the containment structure (100) between the distal end (102) and the proximal end (104) of the containment structure (100) with a total resistance R(260), the vertical secondary portion (260) having a distal end (262) and a proximal end (264):
(iii) a horizontal shunt portion (290) interconnecting the distal ends (212, 262) of the vertical primary and secondary portions (210, 260) with a total resistance R(290), and
the sensor (200) having a total sensor resistance R(200) equal to the sum of the resistances R(210), R(290) and R(260).

C) an interface device (300) having an interior interface portion (310) located substantially in the containment structure interior (106), and an exterior interface portion (320) located substantially external to the containment structure (100), wherein the interior interface portion (310) is connected to a portion of the primary portion (210) and a portion of the secondary portion (260), and wherein the measurement signal (202) is transmitted between the interior interface portion (310) and the exterior interface portion (320).

34. The liquid measurement device (1) of claim 33, wherein the containment structure (100) includes a variable cross-section portion (140), the vertical primary portion (210) of the sensor (200) having a variable resistance per unit length section (230) located within the variable cross-section portion of the containment structure.

35. The liquid measurement device (1) of claim 34 wherein the vertical secondary portion (260) of the sensor (200) has a variable resistance per unit length section (280) located within the variable cross-section portion of the containment structure.

36. The liquid measurement device (1) of claim 35 wherein the containment structure (100) includes a constant cross-section portion (130) having a constant cross-section (132), the vertical primary portion (210) of the sensor having a constant resistance per unit length section (220) located within the constant cross-section portion of the containment structure, the vertical secondary portion (260) having a constant resistance per unit length section (270) located within the constant cross-section portion of the containment structure.

37. The liquid measurement device (1) of claim 35 wherein the proximal ends (214, 264) of the vertical primary and secondary portions (210, 260) convey the sensor resistance R(200) to an external circuit for measurement of liquid height (14), the total sensor resistance R(200) remaining constant when there is no fluid in the containment structure, the total sensor resistance R(200) decreasing as fluid covers first the shunt resistor (290) and then covers increasing lengths of the vertical primary and secondary portions (210, 260), the variable resistance per unit length sections (230, 280) of the vertical primary and secondary portions (210, 260) having a predetermined variation in the resistance per unit length to account for variations in the cross-sectional area of the variable cross-section containment structure whereby the predetermined variation in resistance per unit length renders a linear output signal (202).

38. The liquid measurement device (1) of claim 33 wherein the total resistance R(290) of the horizontal shunt portion (290) is at least 0.5% of the total sensor resistance R(200) of the sensor (200).

39. The liquid measurement device (1) of claim 33 wherein the vertical primary portion (210), the vertical secondary portion (260) and the horizontal shunt portion (290) are one continuous electrode.

* * * * *